United States Patent
Schlosser et al.

(10) Patent No.: US 10,232,194 B2
(45) Date of Patent: Mar. 19, 2019

(54) MANIPULATION OF IMAGING PROBE DURING MEDICAL PROCEDURE

(71) Applicant: The Board of Trustees of the Leland Stanford Junior University, Stanford, CA (US)

(72) Inventors: Jeffrey S. Schlosser, Mountain View, CA (US); Dimitre H. Hristov, Stanford, CA (US); J. Kenneth Salisbury, Jr., Mountain View, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 821 days.

(21) Appl. No.: 14/417,480

(22) PCT Filed: Jul. 29, 2013

(86) PCT No.: PCT/US2013/052582
§ 371 (c)(1),
(2) Date: Jan. 26, 2015

(87) PCT Pub. No.: WO2014/018983
PCT Pub. Date: Jan. 30, 2014

(65) Prior Publication Data
US 2015/0209599 A1  Jul. 30, 2015

Related U.S. Application Data

(60) Provisional application No. 61/676,429, filed on Jul. 27, 2012, provisional application No. 61/799,385, filed on Mar. 15, 2013.

(51) Int. Cl.
*A61N 5/10* (2006.01)
*A61B 8/08* (2006.01)
(Continued)

(52) U.S. Cl.
CPC ............ *A61N 5/1039* (2013.01); *A61B 6/032* (2013.01); *A61B 6/4417* (2013.01);
(Continued)

(58) Field of Classification Search
CPC .. A61N 5/1039; A61N 5/1082; A61N 5/1049; A61N 2005/1058; A61B 6/4417;
(Continued)

(56) References Cited

U.S. PATENT DOCUMENTS 9,572,545 B2 * 2/2017 Chen ...................... A61B 8/085
2001/0013764 A1 8/2001 Blumenkranz et al.
(Continued)

OTHER PUBLICATIONS

Schlosser et al.; U.S. Appl. No. 14/416,482 entitled "Manipulation of imaging probe during medical procedure," filed Jan. 22, 2015.
(Continued)

*Primary Examiner* — Sanjay Cattungal
(74) *Attorney, Agent, or Firm* — Shay Glenn LLP

(57) ABSTRACT

An imaging probe manipulator for use during a medical procedure includes a first manipulator linkage having a connector configured to attach to an imaging probe, a second manipulator linkage coupled to the first manipulator linkage at a first joint a third manipulator linkage coupled to the first or second manipulator linkage at a second joint. The first joint or the second joint has a degree of freedom. The imaging probe manipulator includes a force control transmission linked to the degree of freedom. The force control transmission component is configured to maintain a predetermined force on the imaging probe when the imaging probe is in contact with a patient.

23 Claims, 40 Drawing Sheets

(51) Int. Cl.
*A61B 8/00* (2006.01)
*A61B 6/03* (2006.01)
*A61B 6/00* (2006.01)

(52) U.S. Cl.
CPC ............ *A61B 6/5247* (2013.01); *A61B 8/085* (2013.01); *A61B 8/0875* (2013.01); *A61B 8/4218* (2013.01); *A61B 8/4263* (2013.01); *A61B 8/4416* (2013.01); *A61B 8/4444* (2013.01); *A61B 8/5261* (2013.01); *A61B 8/54* (2013.01); *A61N 5/1049* (2013.01); *A61N 5/1082* (2013.01); *A61B 8/4245* (2013.01); *A61N 2005/1058* (2013.01)

(58) Field of Classification Search
CPC ... A61B 6/5247; A61B 8/4416; A61B 8/5261; A61B 6/032; A61B 8/4444; A61B 8/0875; A61B 8/4263; A61B 8/4218; A61B 8/085; A61B 8/54; A61B 8/4245
USPC .................................................. 600/407–480
See application file for complete search history.

(56) References Cited

U.S. PATENT DOCUMENTS

| | | | |
|---|---|---|---|
| 2008/0249403 | A1 | 10/2008 | Suri et al. |
| 2010/0274087 | A1 | 10/2010 | Diolaiti et al. |
| 2011/0277775 | A1* | 11/2011 | Holop ............... A61B 17/3423 128/849 |
| 2012/0095336 | A1 | 4/2012 | Dogra et al. |
| 2013/0085387 | A1* | 4/2013 | Chen ..................... A61B 8/085 600/439 |
| 2015/0165234 | A1* | 6/2015 | Bharat ................ A61N 5/1064 600/427 |

OTHER PUBLICATIONS

Hartov et al.; Adaptive spatial calibration of a 3D ultrasound system; Med. Phys.; 37(5); pp. 2121-2130; May 2010.
Schlosser et al.; Online image-based monitoring of soft-tissue displacement for radiation therapy of the prostate; Int. J. Radiation Oncol. Biol. Phys. 83(5); pp. 1633-1640; Aug. 1, 2012.
Schlosser; Robotic ultrasound image guidance for radation therapy; PhD. of Philosophy; Dissertation; Stanford University; Mar. 2013.
Schlosser et al.; Telerobotic system concept for real-time soft-tissue imaging during radiotherapy beam delivery; Med. Phys.; 37(12); pp. 6357-6367; Dec. 2010.
Dillenseger et al.; Fast simulation of ultrasound images from a ct volume; 39(2); pp. 180-186; Feb. 2009.
Dimitre; Real-time telerobotic 3d ultrasound for soft-tissue guidance concurrent with beam delivery; AAPM 54th Annual meeting & Exhibition; Charlotte, NC; 11 pages; Jul. 29, 2012-Aug. 2, 2012.
Schlosser et al.; Hybrid x-ray/ultrasound imaging approach for patient postitioning and real-time tracking in igrt; Med. Phys.; 38(6); pp. 3389-3390; Jun. 2011.

* cited by examiner

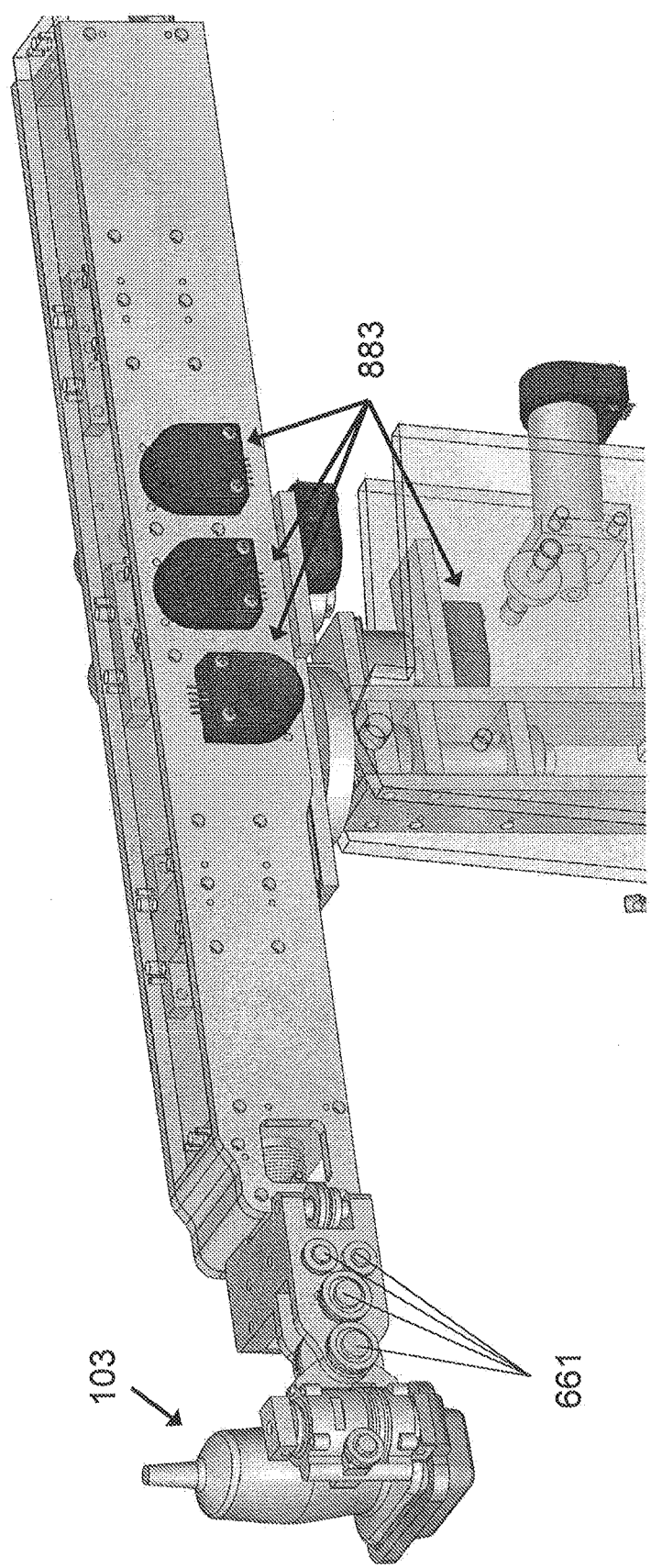

101

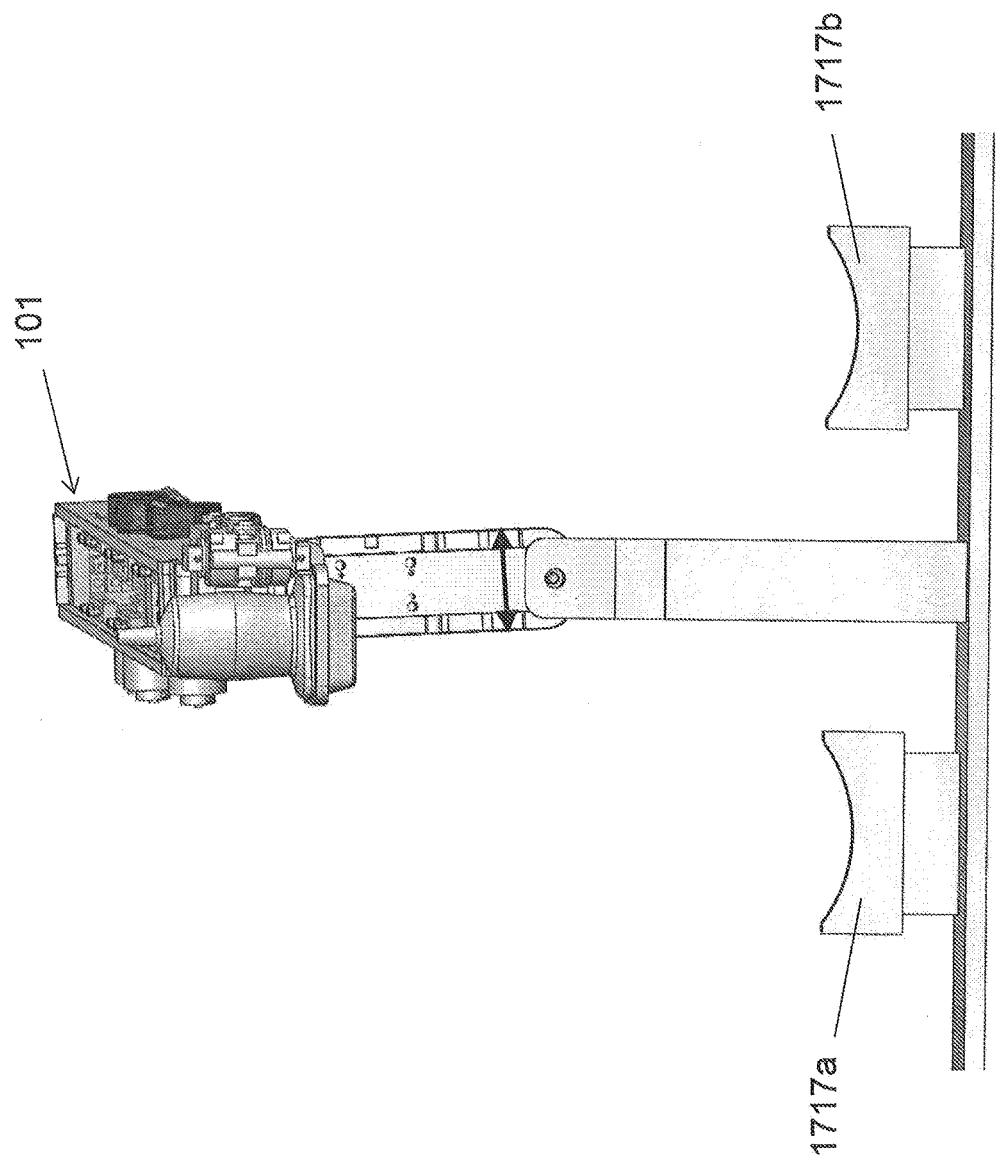

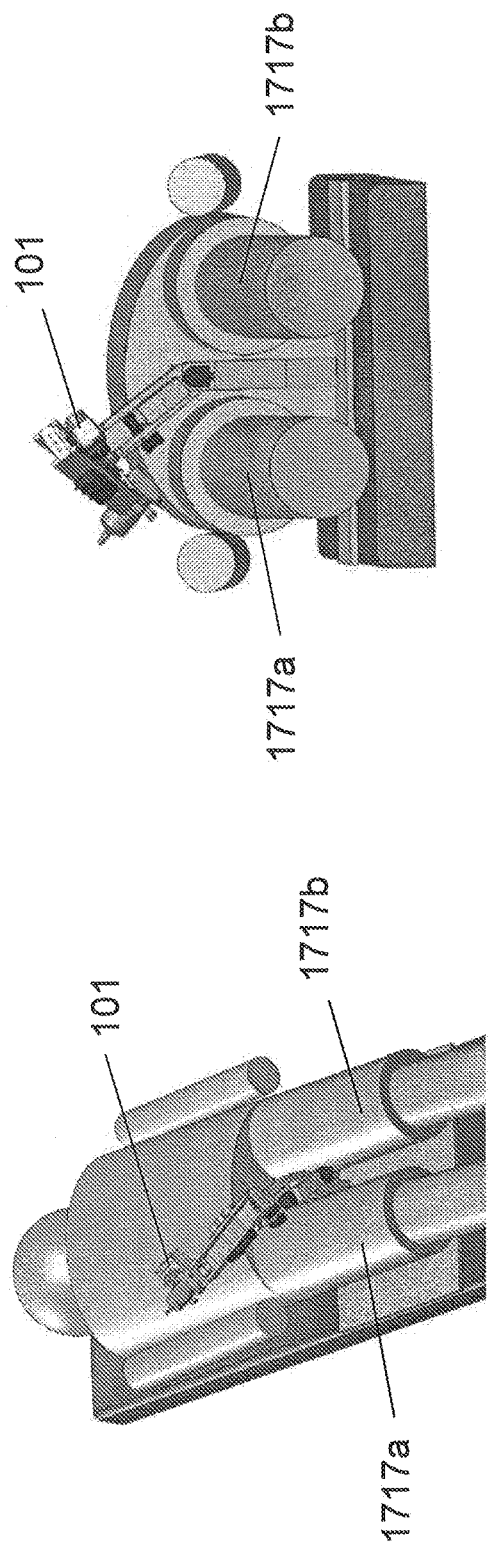
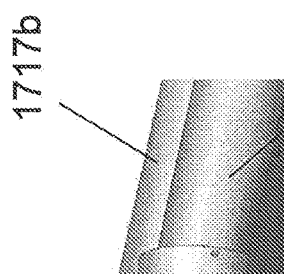
FIG. 18b
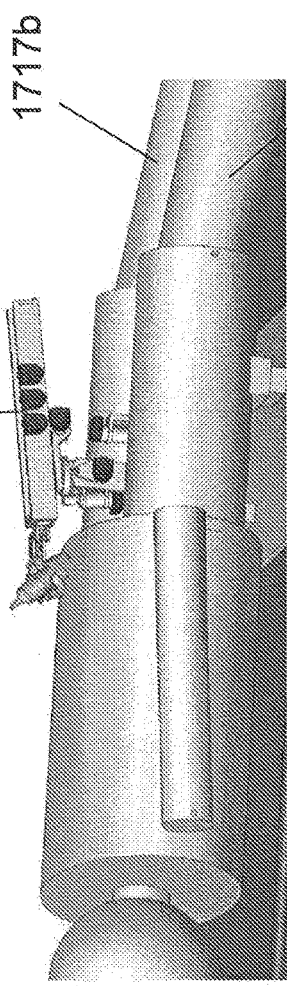
FIG. 18c
FIG. 18a

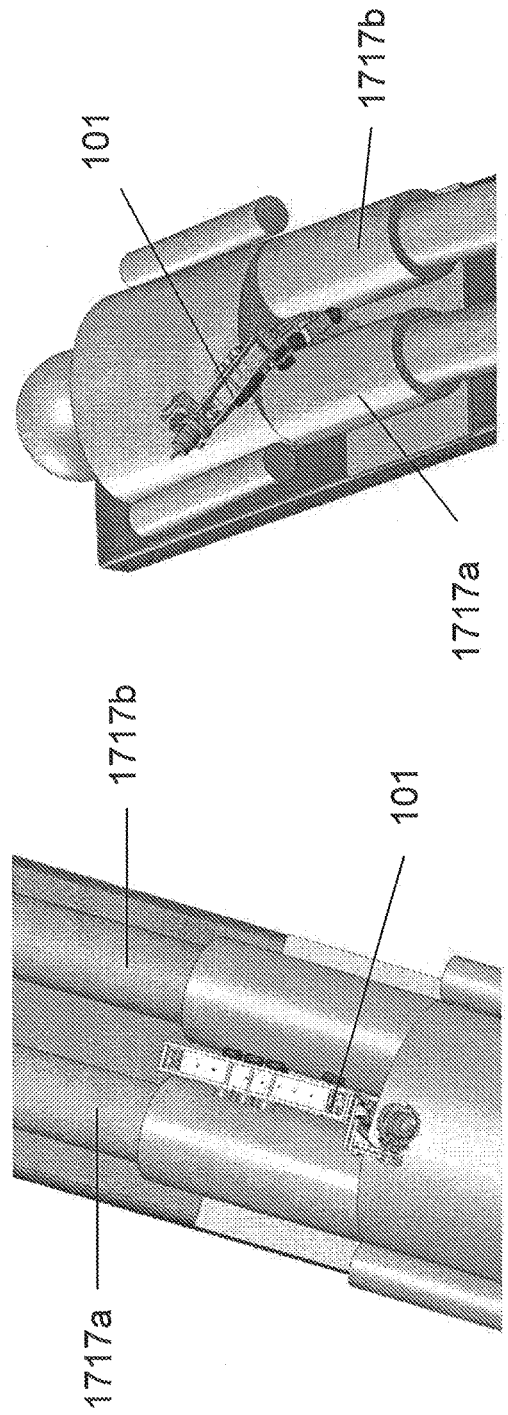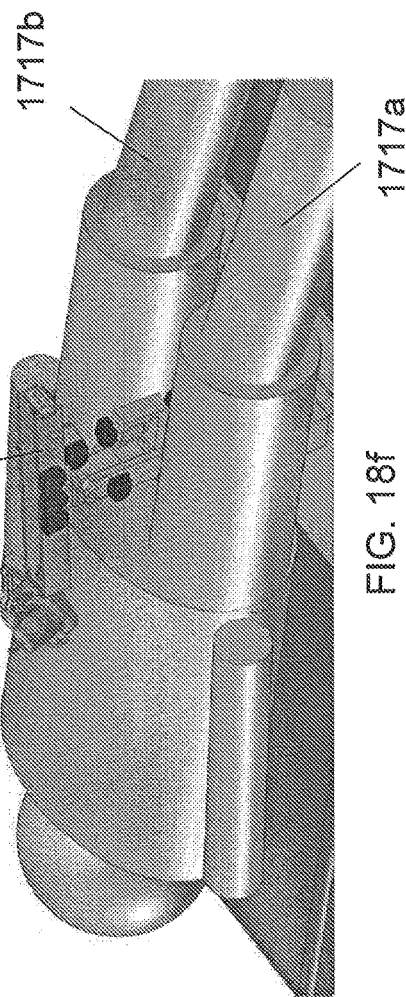
FIG. 18d
FIG. 18e
FIG. 18f

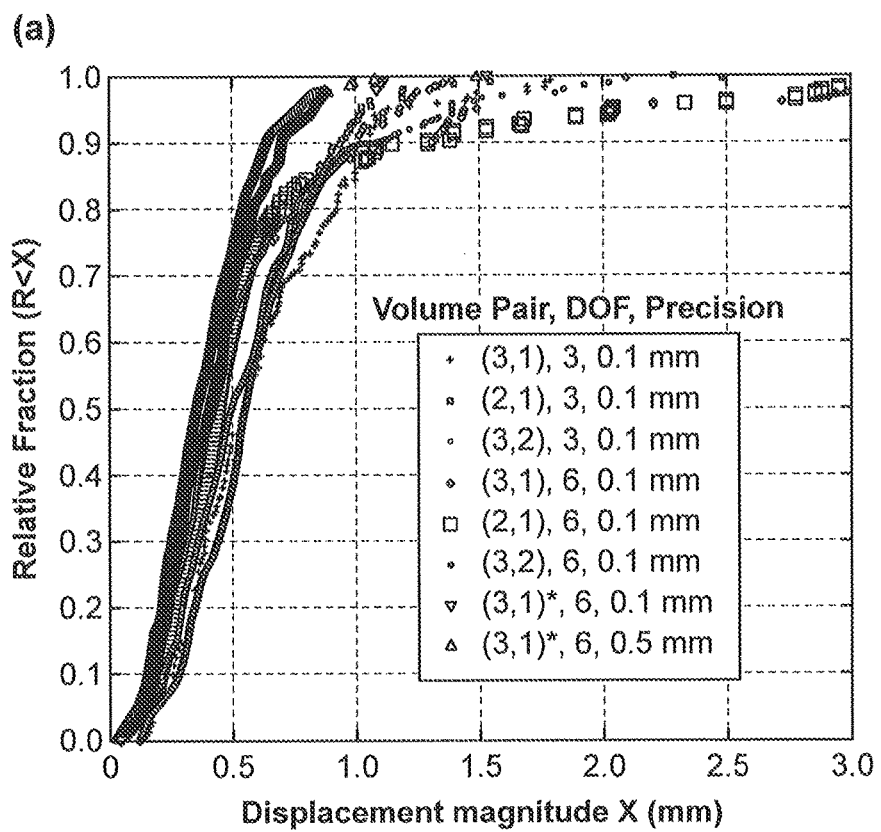
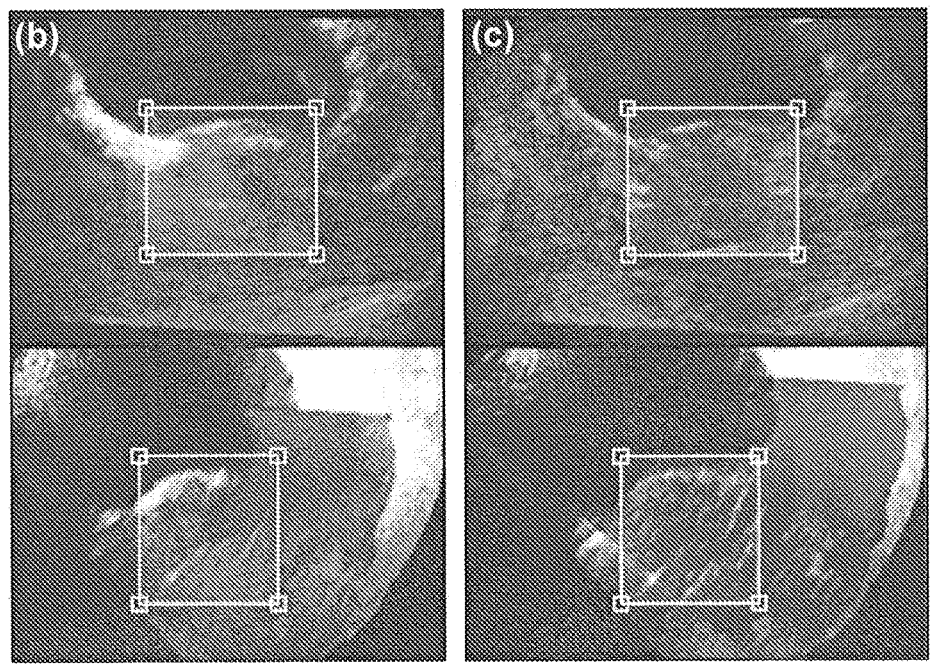
FIG. 22

MANIPULATION OF IMAGING PROBE DURING MEDICAL PROCEDURE

CROSS REFERENCE TO RELATED APPLICATIONS

This application claims priority to U.S. Provisional Patent Application No. 61/676,429, filed on Jul. 27, 2012 and titled "ROBOTIC ULTRASOUND IMAGE GUIDANCE IN RADIOTHERAPY," which is incorporated by reference in its entirety. This application also claims priority to U.S. Provisional Patent Application No. 61/799,385, filed on Mar. 15, 2013 and titled "RADIOTHERAPY TREATMENT PLANNING TECHNIQUES," which is incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

External Beam Radiation Therapy (EBRT) is used in the disease management of more than half of all cancer patients worldwide. Recent advances in EBRT delivery regimens (e.g., Stereotactic Body Radiation Therapy) and tumor detection methods (e.g., molecular imaging) pave the way for the treatment of increasingly small lesions with increasingly high ablative radiation doses to maximize local control rates. In light of these trends, high dose conformality is important for delivering curative dose to the target while sparing surrounding healthy structures. Random and quasi-periodical anatomy motion during beam delivery poses a fundamental threat to realizing such conformality, and thus restricts the curative potential of EBRT.

Existing and emerging technologies for localizing abdominal targets during beam delivery employ tracking of implanted fiducial markers, tracking of external surrogates, or guidance via magnetic resonance images. However, these technologies cannot provide real-time, volumetric, non-invasive, markerless, soft-tissue image guidance capabilities with existing radiation delivery platforms. Thus, a significant opportunity exists to improve the widespread technical capability and clinical outcomes of EBRT.

Several key issues remain in the design of a system configured to image during radiotherapy, including: (1) reliably obtaining 3D ultrasound images over extended times with minimal interference to the radiotherapy workflow; (2) improving processing times for quantitative interpretation of ultrasound data; and (3) avoiding interference of the ultrasound transducer with radiation delivery. The system described herein is intended to solve some of these problems.

SUMMARY OF THE DISCLOSURE

In general, in one embodiment, an imaging probe manipulator for use during a medical procedure includes a first manipulator linkage having a connector configured to attach to an imaging probe, a second manipulator linkage coupled to the first manipulator linkage at a first joint, and a third manipulator linkage coupled to the first or second manipulator linkage at a second joint. The first joint or the second joint has a degree of freedom. The imaging probe manipulator includes a force control transmission component linked to the degree of freedom. The force control transmission component is configured to maintain a pre-determined force on the imaging probe when the imaging probe is in contact with a patient.

This and other embodiments can include one or more of the following features. The force control transmission component can be a series elastic force control component. The series elastic force control component can include a plurality of springs. The series elastic force control transmission component can include a motor configured to maintain the pre-determined force by adjusting the tension in each of the plurality of springs. The imaging probe manipulator can further include a position encoder coupled to at least one of the springs in the plurality of springs, and the motor can be operated in response to an output of the position encoder. The series elastic force control transmission component can include a manual dial configured to control the amount of elasticity in each of the plurality of springs. The imaging probe can be an ultrasound probe. The connector can be configured to removably receive a first imaging probe while the imaging probe manipulator is in use during radiation therapy and removably receive a second imaging probe while the imaging probe manipulator is in use during a medical imaging procedure. The first probe can be operable and the second probe can be inoperable. The second probe can be made of substantially non-metallic components. At least a portion of the manipulator linkages adjacent to the image probe can be made of substantially non-metallic components. At least a portion of the manipulator linkages adjacent to the imaging probe can be made from low radiation absorbing materials. The imaging probe manipulator can further include at least one brake on the first or second joint. The imaging probe manipulator can further include at least one encoder coupled with the brake so as detect position information of the brake. The encoder can be a laser encoder. The at least one brake can be an electromagnetic brake. The imaging probe manipulator can further include a controller configured to receive and store position information regarding the at least one brake. The memory of the electronic controller can include instructions to operate the at least one brake based on the stored position information. The controller can be configured to receive the position information while the manipulator is in use during a medical imaging procedure, and the controller instructions to operate can be adapted for use while the manipulator is in use during a medical therapy based upon the medical imaging procedure.

In general, in one embodiment, an imaging probe manipulator for use during a medical procedure includes a first manipulator linkage configured to be coupled to an imaging probe, a plurality of linkages and joints coupled to the first manipulator linkage arranged to provide at least five degree of free of movement of the imaging probe, a plurality of brakes coupled to the joints to lock at least four of the degrees of freedom; and an encoder associated with each brake, and a force transmission component. The force control transmission component is configured to maintain a pre-determined force on the imaging probe when the imaging probe is in contact with a patient. The encoder is configured to detect the position of the associated brake.

This and other embodiments can include one or more of the following features. The force transmission component can be configured to actuate along an axis that is redundant to one of the degrees of freedom associated with the brakes.

In general, in one embodiment, a method of planning the delivery of a radiation therapy using an input from a portable imaging probe of a patient's target anatomy includes positioning the portable imaging probe connected to an imaging probe manipulator so that the imaging probe is in a desired position for taking an image of the patient's target anatomy, imaging a portion of the patient's target anatomy using the portable imaging probe while the imaging probe is in the desired position, conducting a planning medical imaging scan of a portion of a patient's anatomy, and planning radiation therapy delivery while accounting for the presence of the portable imaging probe.

This and other embodiments can include one or more of the following features. The imaging probe manipulator can have a plurality of joints. Positioning the portable imaging probe can include locking at least some of the joints in place. The method can include a storing positions of the joints after locking at least some of the joints in place. The step of conducting a planning medical imaging scan can be performed while the portable imaging probe is in the desired position. The positioning step or the imaging step can be determined using knowledge of a geometrical configuration of a radiation delivery system to be used to deliver a therapy to the patient's target anatomy. The positioning step or the imaging step can be determined using knowledge of a geometrical configuration of a potential radiotherapy beam arrangement to be used during therapy delivery to the patient's target anatomy. The method can include using simulated portable probe images of a portion of the patient's target anatomy to inform positioning the portable probe prior to radiation therapy. A low-dose CT scan can be used to simulate images from the portable probe. The method can include using bone or gas data from the imaging scan of a portion of the patient's target anatomy to inform positioning the portable probe prior to radiation therapy. In the positioning step, the manipulator can lock or provide resistance to various joints to prevent the probe operator from moving the probe to particular positions that could interfere with the treatment delivery device or radiation beams. In the positioning step, the manipulator can actively control various joints to push the probe towards particular positions that are determined to be suitable according to treatment geometry or simulated images. The method can include using a visualization platform coupled to the manipulator to provide position, pose, or pressure information during the positioning, imaging, or planning steps. The method can include using a visualization platform coupled to the manipulator to detect potential imaging probe and imaging probe manipulator interference with one or both of a physical treatment system component and/or a planned treatment beam to be used in later radiation therapy of the patient target anatomy. The method can include using an output from the visualization platform for positioning of the imaging probe and the imaging probe manipulator to avoid a physical treatment system component and/or the planned treatment beam. The method can include using a plurality of outputs from the visualization platform for positioning of the imaging probe and the imaging probe manipulator, each one of the outputs corresponding to a positioning of the probe and manipulator for a portion of the radiation therapy such that for beams during that portion the probe and the manipulator avoid the treatment system component and the planned treatment beam. The method can include delivering a first portion of a radiation therapy to a patient where the manipulator and the probe are in one of the corresponding outputs and delivery of a second portion of a radiation therapy to a patent where the manipulator and the probe are in another one of the corresponding outputs. The planning step can be performed with an inoperable probe including non-metallic materials that can be coupled to the imaging probe manipulator. The inoperable probe can include different densities to indicate different densities in the actual imaging probe so that areas of high density can be avoided in the planning process. The imaging probe can be connected to the imaging probe manipulator through a connector, and the connector can include a cup having a gel or fluid therein. The conducting step can be performed with an imaging probe coupled to the imaging probe manipulator and the planning medical imaging scan of a portion of a patient's anatomy can include a portion of a density model of the imaging probe. The conducting step can be performed with an imaging probe holder coupled to the imaging probe manipulator, and the planning medical imaging scan of a portion of a patient's anatomy can include a portion of a density model of an imaging probe to be coupled to the imaging probe holder during a later delivery of radiation therapy. The method can include applying pressure to the patient target anatomy using a plurality of probe pressures and recording deformations of the patient target anatomy resulting from each pressure in the plurality of pressures and incorporating this information to computationally deform the patient CT scan to accurately reproduce the deformations that can be seen during actual treatment. The method can include modifying the imaging data collected during the conducting step based on one or more of the recorded deformations.

In general, in one embodiment, a method of synchronizing the timing of two different sensors includes: mounting a first sensor and a second sensor to a sinusoidal motion stage; recording the sensor outputs of the first sensor and the second sensor; determining a phase shift between the outputs of the first and second sensor; and using the determined phase shift to calculate a temporal delay between the sensors.

In general, in one embodiment, a method of tracking tissue includes: collecting a plurality of three-dimensional ultrasound scans of a tissue a set time intervals; collecting a plurality of two-dimensional ultrasound scans of the tissue between the set time intervals; and integrating the three-dimensional ultrasound scans and the two-dimensional ultrasound scans to estimate a position of the tissue.

In general, in one embodiment, a method of determining the position of a portable imaging probe against a patient includes obtaining images from a portable probe from a plurality of candidate probe positions, simulating the obtained images using properties of a prior imaging scan and geometrical knowledge of the candidate probe positions, and evaluating the simulated images to determine a position for the probe.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 5a shows pulleys and position encoders on a probe manipulator.

FIG. 17 shows mounting of a probe manipulator between a patient's legs.

FIGS. 18a-18g show various imaging positions for a probe when a probe manipulator is mounted between a patient's legs.

FIG. 21a shows detected prostate displacements, rotations, and false positive (FP) rate vs. image parameter thresholds. FIG. 21b shows a comparison of external marker and internal ultrasound signal for liver feature tracking.

FIG. 22a shows cumulative distributions of total residual displacement after 2165 MI registrations per prostate volume pair. The registered pairs are indicated along with the number of DOF used for the registration. Figures b-c show axial and sagittal overlays of 3D prostate data set before (b) and after (c) MI registration.

DETAILED DESCRIPTION

Figure 1:
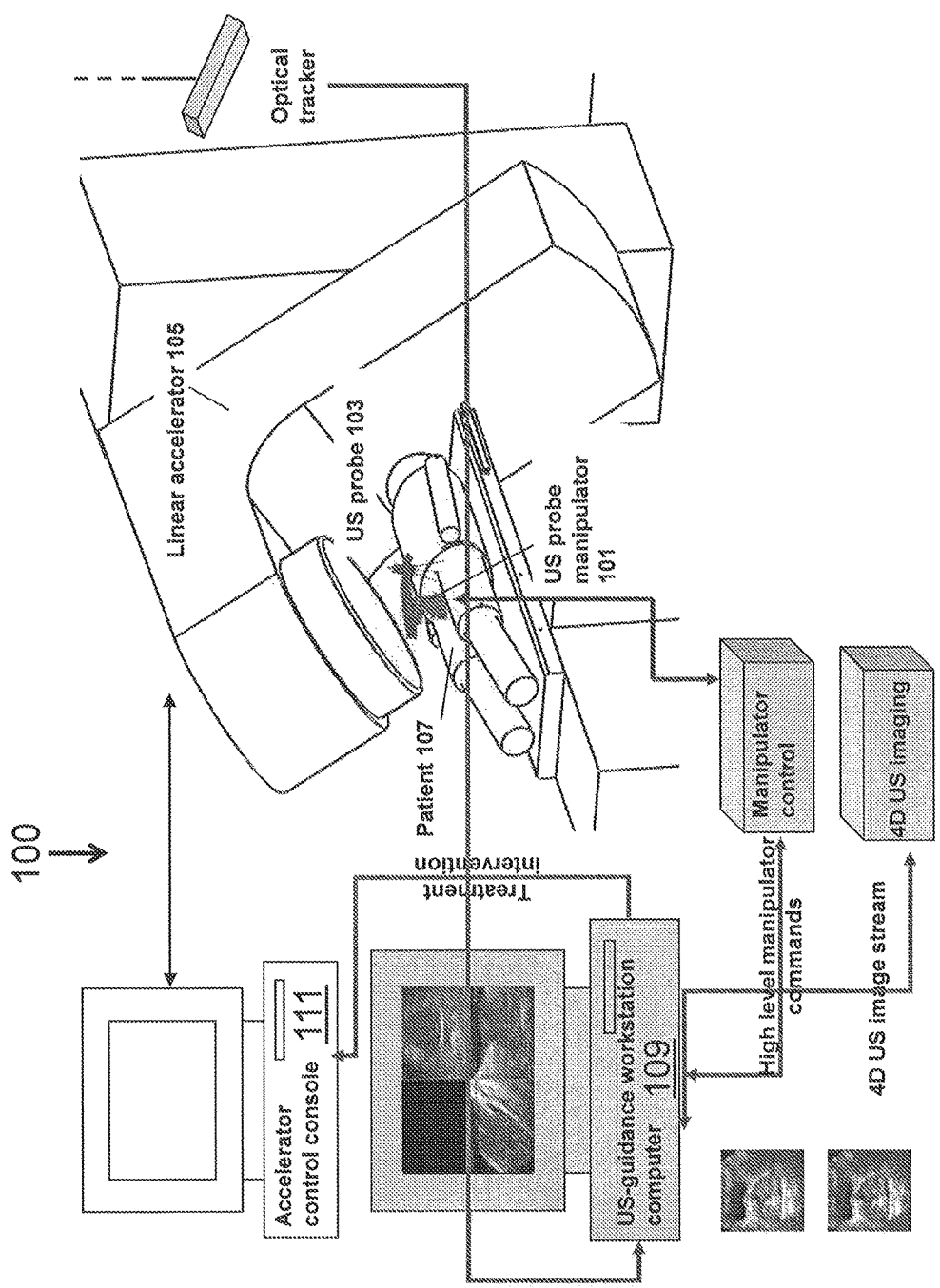
FIGS. 1 and 2 show a system for providing ultrasound during radiation therapy.
Figure 2:
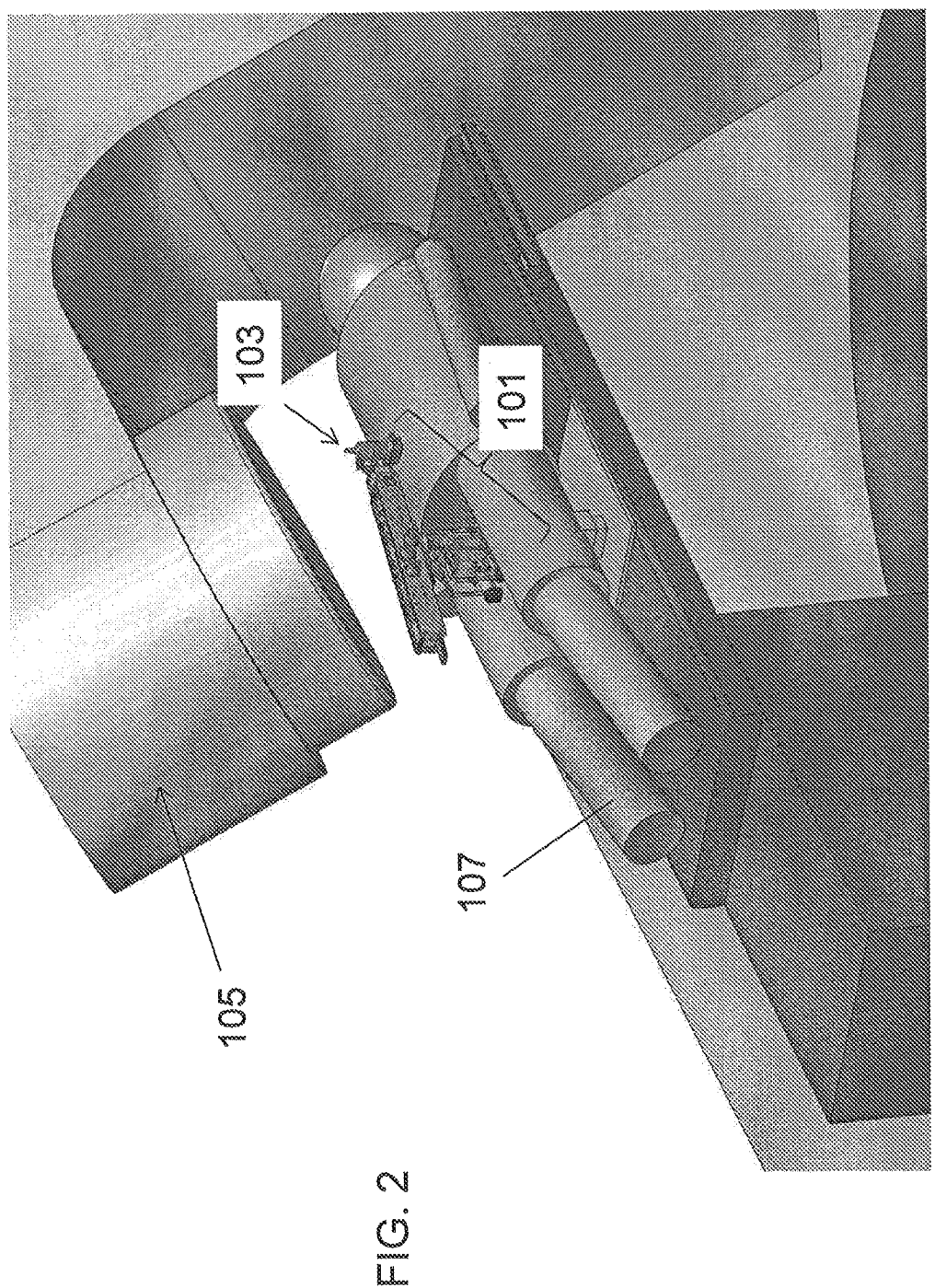

Referring to FIGS. 1 and 2, a system 100 for providing ultrasound during radiation therapy can include a probe manipulator 101 having several degrees of freedom (DOF), such as more than two, more than three, more than four, or more than five degrees of freedom, such as approximately six, seven, or eight degrees of freedom. The probe manipulator 101 can be connected to an ultrasound probe 103, such as a 4D ultrasound probe, that can be used in combination with a radiation therapy device, such as a linear accelerator (LINAC) machine 105, to take ultrasound (US) images during radiation beam therapy. In some embodiments, the probe manipulator 101 can be designed to control the pose and pressure of the probe 103 against the patient 107. Precise spatial localization of 3D ultrasound images can be achieved via tracking, such as continuous multiple degree of freedom (DOF) infrared optical tracking of the probe's position. Before treatment, the patient 107 can be positioned in the frame of the LINAC 105 according to planned dose distributions using inter-modality registration of on-site US images and hardware fused US/CT images collected in simulation.

Referring to FIG. 1, during treatment beam delivery, soft-tissue targets can be tracked using real-time image-based algorithms computed on 4D data streamed from the ultrasound machine to the workstation computer 109. A treatment intervention signal can be automatically communicated to an accelerator control console 111 of the LINAC machine in order to adjust treatment delivery in accordance with tracked target motion The system 100 described herein advantageously enables minimally-interfering ultrasound imaging of the liver, pancreas, prostate, kidneys, diaphragm, and other organs during radiation beam delivery.

Design of Probe Manipulator

Figure 3:
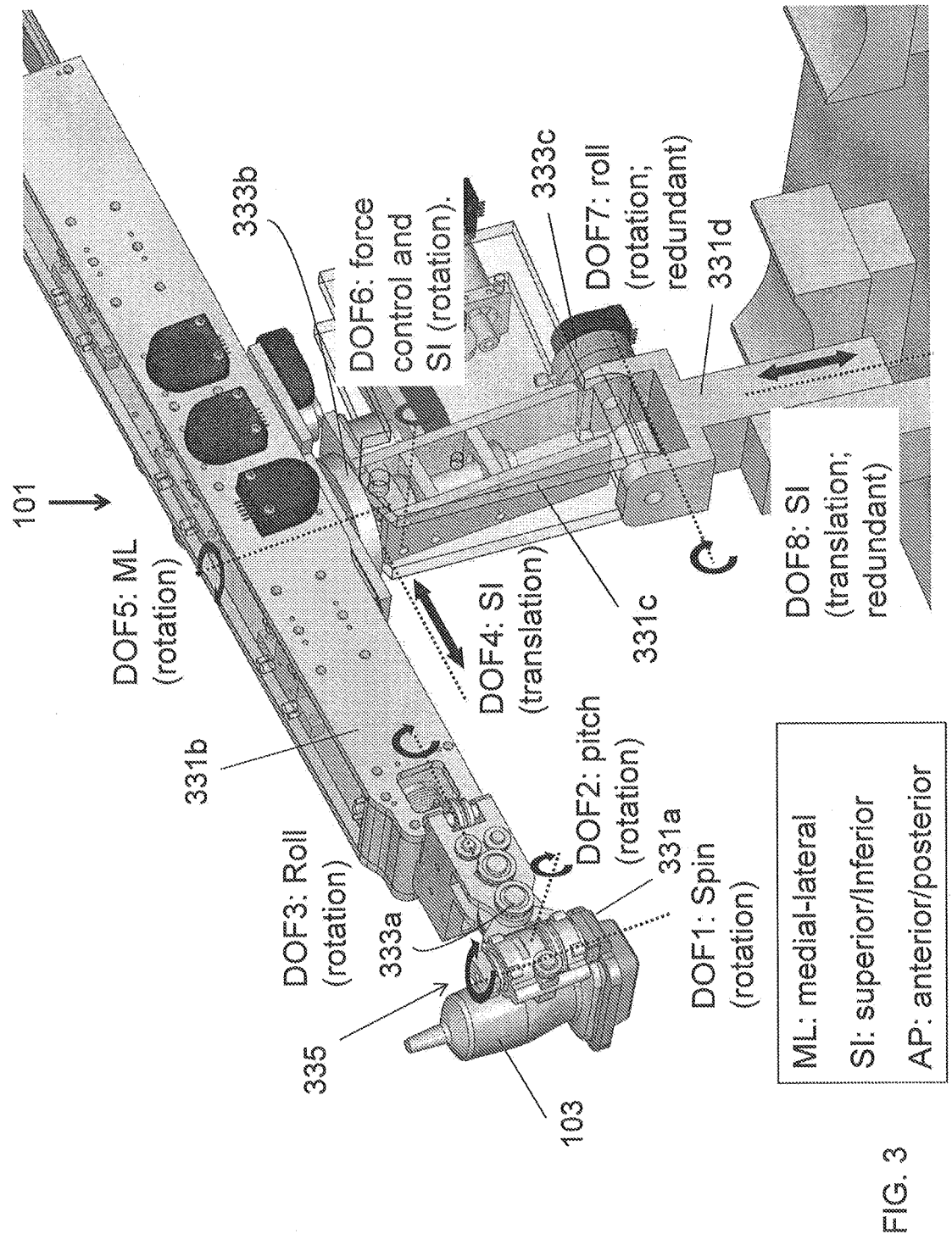
FIG. 3 shows a probe manipulator with multiple degrees of freedom.

Referring to FIG. 3, the probe manipulator 101 can include a plurality of linkages 331, such as four linkages 331a,b,c,d connected together through joints 333, such as three joints 333a,b,c to create three or more degrees of freedom (as discussed further below, eight degrees of freedom are shown in the embodiment of FIG. 3). The distal end of the manipulator 101 can include a wrist 335 and connector configured to allow an ultrasound probe 103 to mount thereto.

Figure 4:
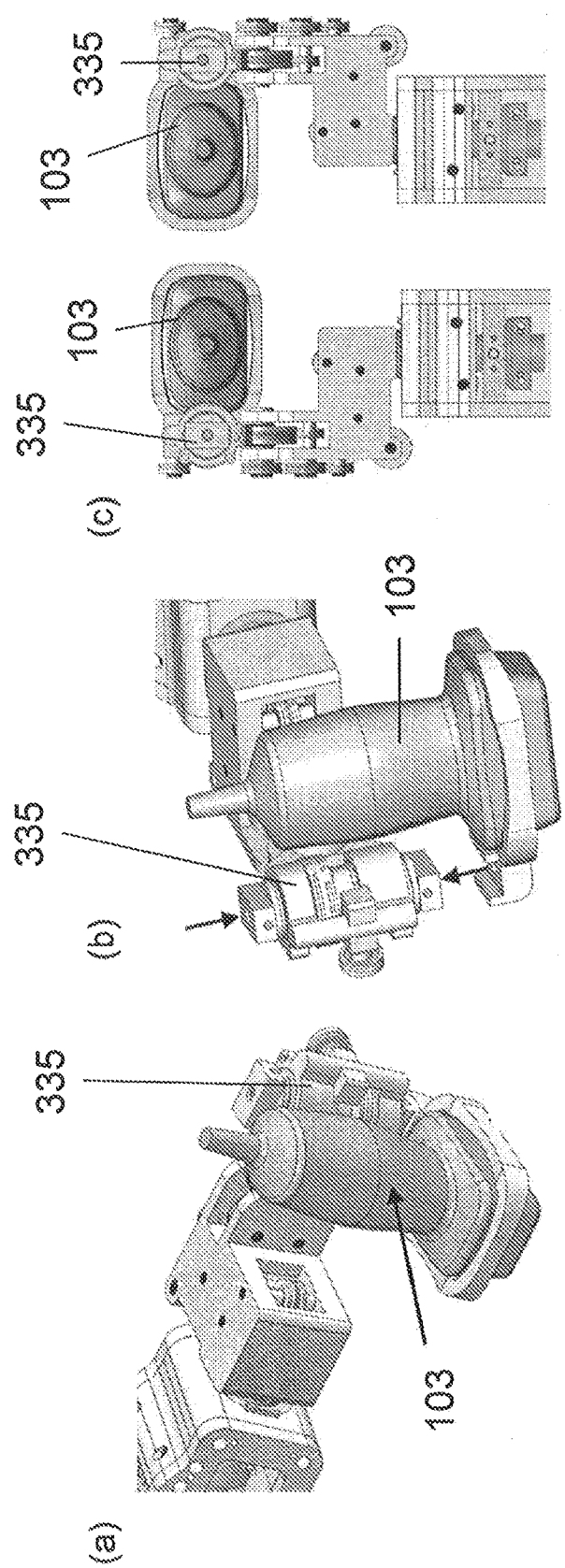
FIGS. 4a-4c show exemplary positions of a wrist of a probe manipulator.
Figure 5B:
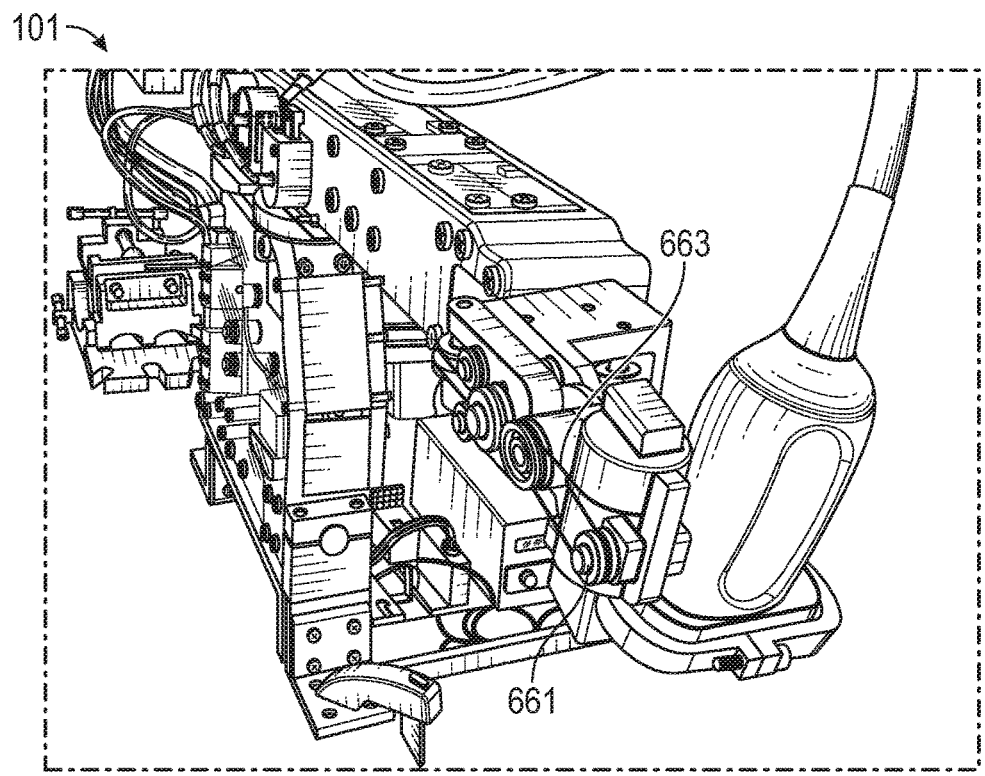
FIGS. 5b-5d show various views of a probe manipulator with cables and pulleys.
Figure 5C:
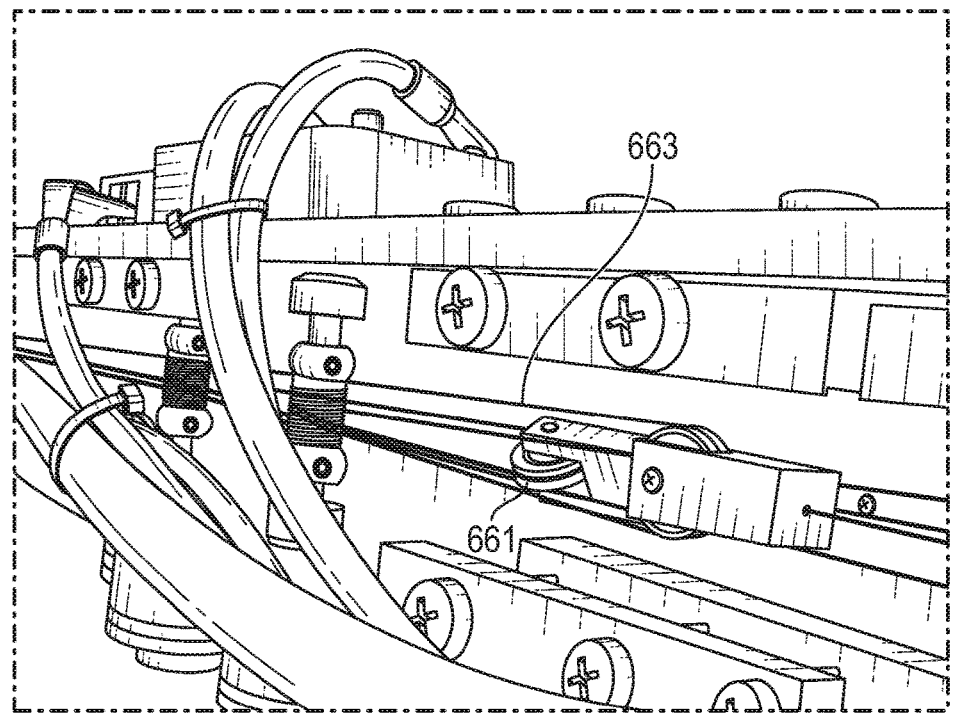
Figure 5D:
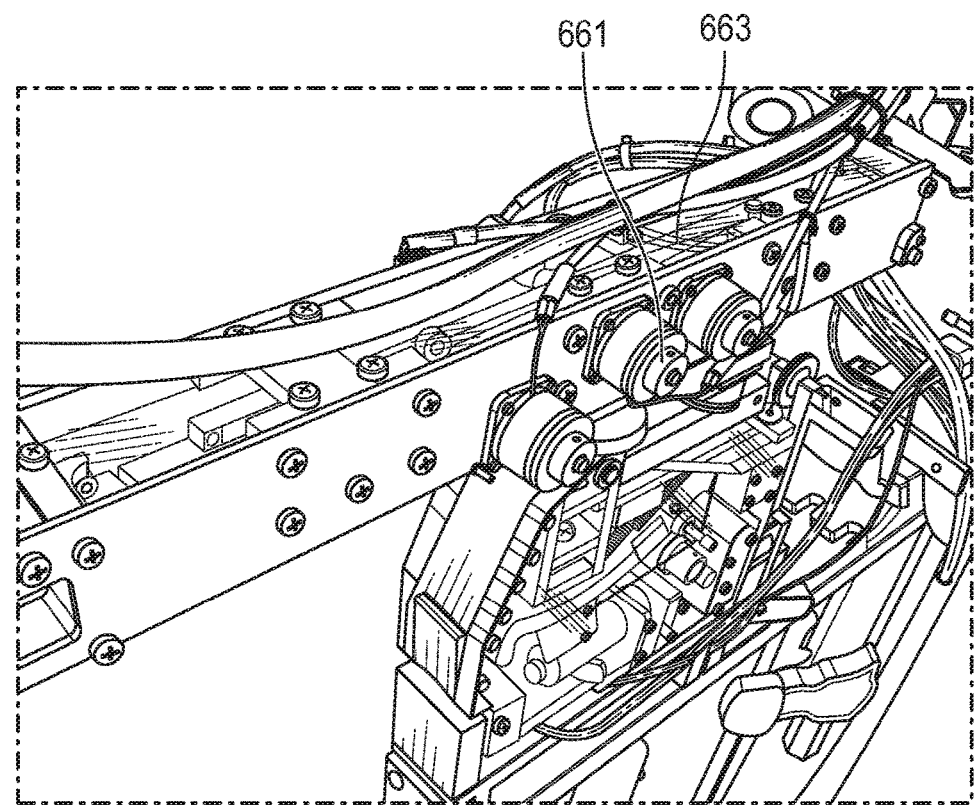

Referring to FIGS. 4a-4c, the multiple degrees of freedom of the manipulator 101 can be used to control the position of the probe 103 to allow for the desired ultrasound image to be taken. As shown in FIGS. 4a-4c, in one embodiment, the wrist 335 (which incorporates DOF1-3 shown in FIG. 3) can include a symmetrical design that allow for the probe 103 to be mounted on either of the blocks shown by the arrows. As a result, the wrist 335 can advantageously be used in either configuration shown in FIG. 5c to accommodate either right-handed or left-handed operators. The wrist 335 is configured to allow the probe to spin about an axis that is parallel, but offset from, the long axis of the probe body.

In some embodiments, the wrist can be designed such that it does not extend vertically above the top of the ultrasound transducer, therefore ensuring maximum clearance between image guidance hardware and the LINAC head.

Figure 35:
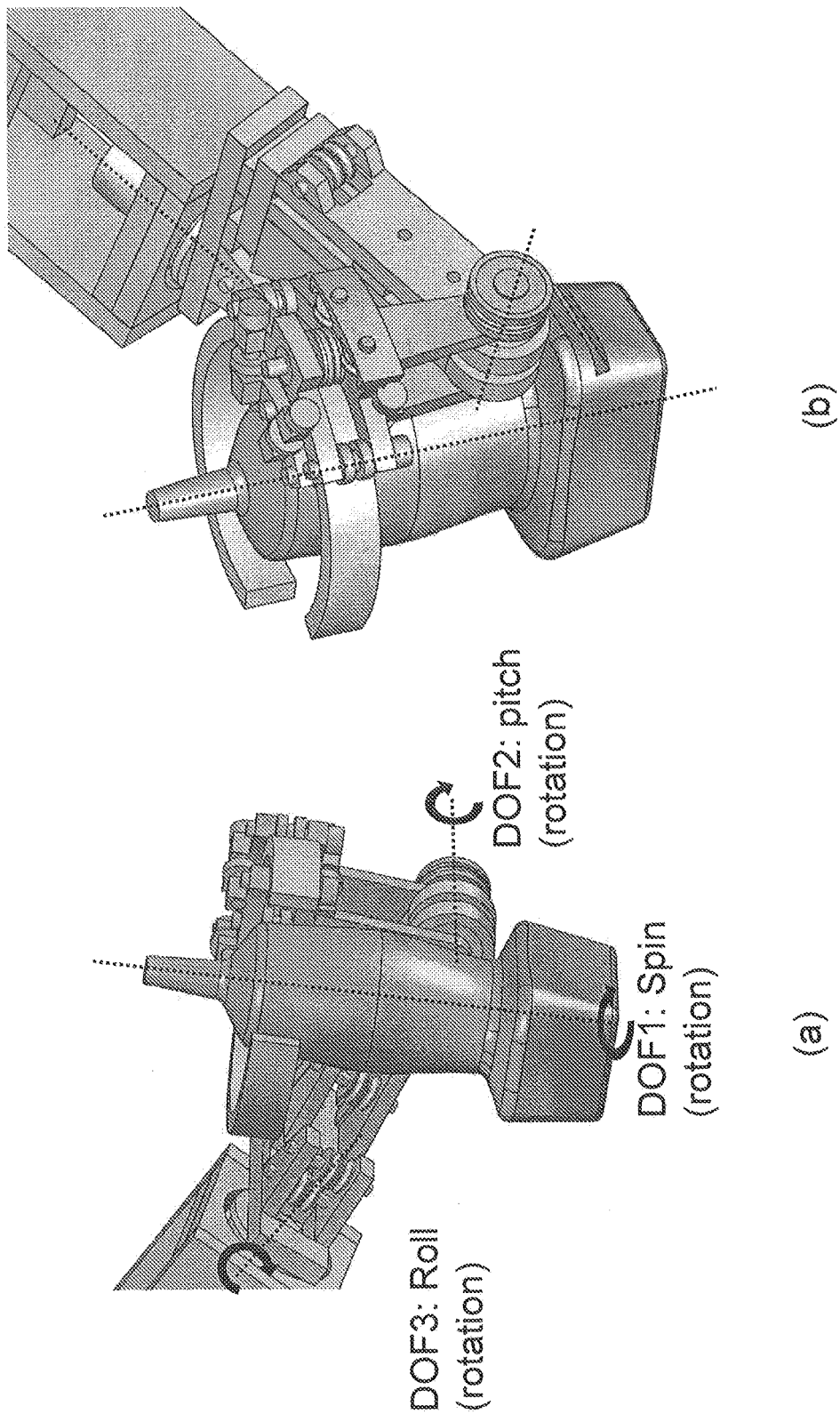
FIG. 35 shows another embodiment of an exemplary wrist of a probe manipulator.

Referring to FIG. 35, another embodiment for a wrist 3535 is shown. The wrist 3535 is configured to allow the probe to spin about the center of the probe, coincident with the long axis of the probe.

Manipulator with Non-Metallic Distal End

One challenge associated with using an ultrasound imaging system during radiation beam therapy is ensuring that approximately the same amount of pressure is placed on a patient during treatment planning (e.g., during a CT scan) as is placed on the patient by the ultrasound probe during radiation treatment. If approximately the same amount of pressure is not applied during treatment as during planning, then the treatment plan can be erroneous, as the ultrasound transducer will place pressure on the patient's anatomy and skew the size/placement of the anatomy relative to the original CT scan. Pressure can be maintained by placing the ultrasound transducer on the patient while the CT scan is being completed. However, to do so, there can be little or no metal in the area of imaging, as metal can cause distortion in the resulting ultrasound image. Eliminating or reducing metallic components at the distal end of the probe manipulator can advantageously reduce absorption of radiation by the manipulator such that it minimally interferes with the treatment delivery.

Accordingly, in one embodiment, at least a distal portion of the probe manipulator can be formed of non-metallic materials. In order to maintain non-metallic parts at the distal end, the joints in the distal end of the probe manipulator can be controlled by cables or other mechanical transmission means connected between actuators or sensors located proximal of the distal portion and/or by non-metallic actuators or sensors. Referring to FIGS. 5a-5d, cables 663, pulleys 661, and position encoders 883 can be used to eliminate or reduce metallic components near the distal end of the manipulator 101.

Figure 6:
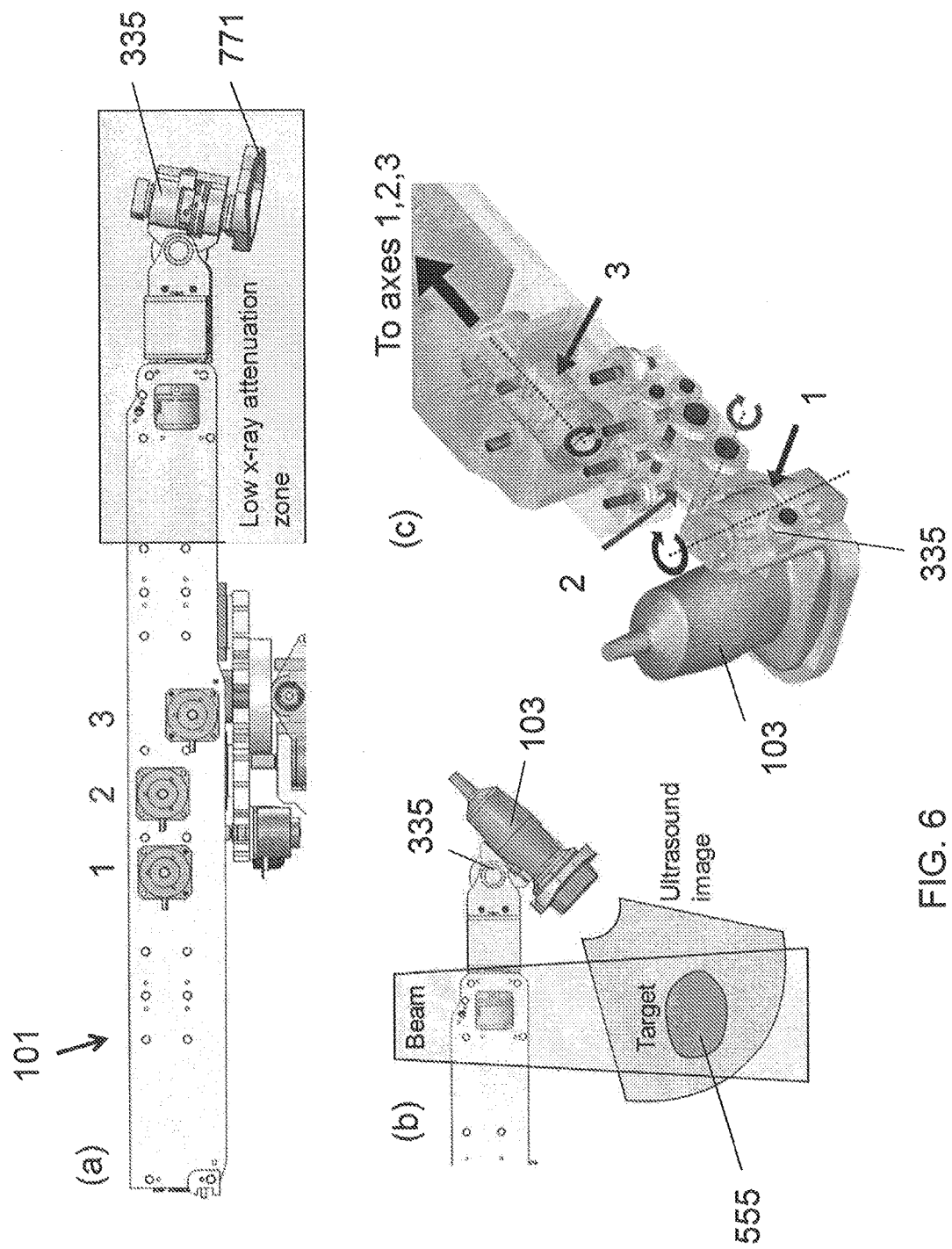
FIGS. 6a-6c show position of non-metallic components in a low z number zone.
Figure 10:
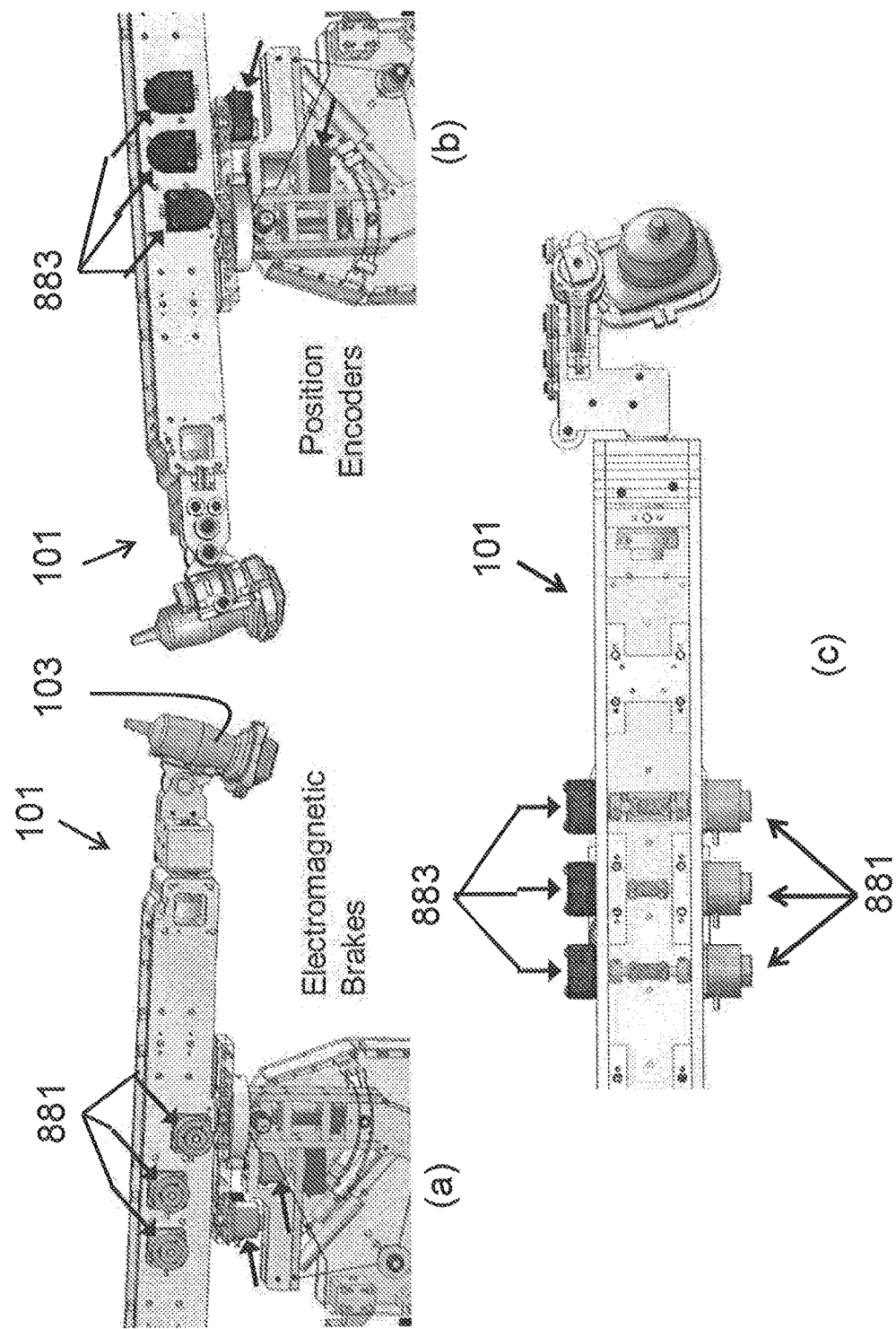
FIGS. 10a-10c show brakes and position encoders on a probe manipulator.

Thus, referring to FIG. 6a, metallic components can be reduced or eliminated in the "low x-ray attenuation zone," i.e., the zone where the materials should have low absorption of radiation. As shown in FIGS. 6a-6c, in one embodiment, the wrist 335 can be plastic (or otherwise non-metallic) and can be coupled to remotely located (i.e. located outside of the z-number zone) actuators, sensors, or encoders through cables 663. The encoders 883 can be seen in FIG. 10—they are opposite to the brakes 881 shown in FIGS. 6a-6c.

In some embodiments, non-metallic brakes or actuators can be used in place of the cable system. For example, pneumatic brakes or laser encoders can be used in place of cables to minimize the amount of metal in the "low x-ray attenuation zone." Thus, sensors that measure rotary or linear movement in combination with a brake (such as a pneumatic brake) to stop motion or a motor that actively causes or impedes motion (such as a laser encoder).

The metal-less area can extend proximally away from the wrist 335 in order to account for the situation shown in FIG. 6b, where the probe 103 is imaging a deep target 555 and pitched back towards the manipulator base. Using remotely-located sensors and/or nonmetallic sensors can advantageously reduce or eliminate the effects of stray radiation on the electronics.

Figure 7A:
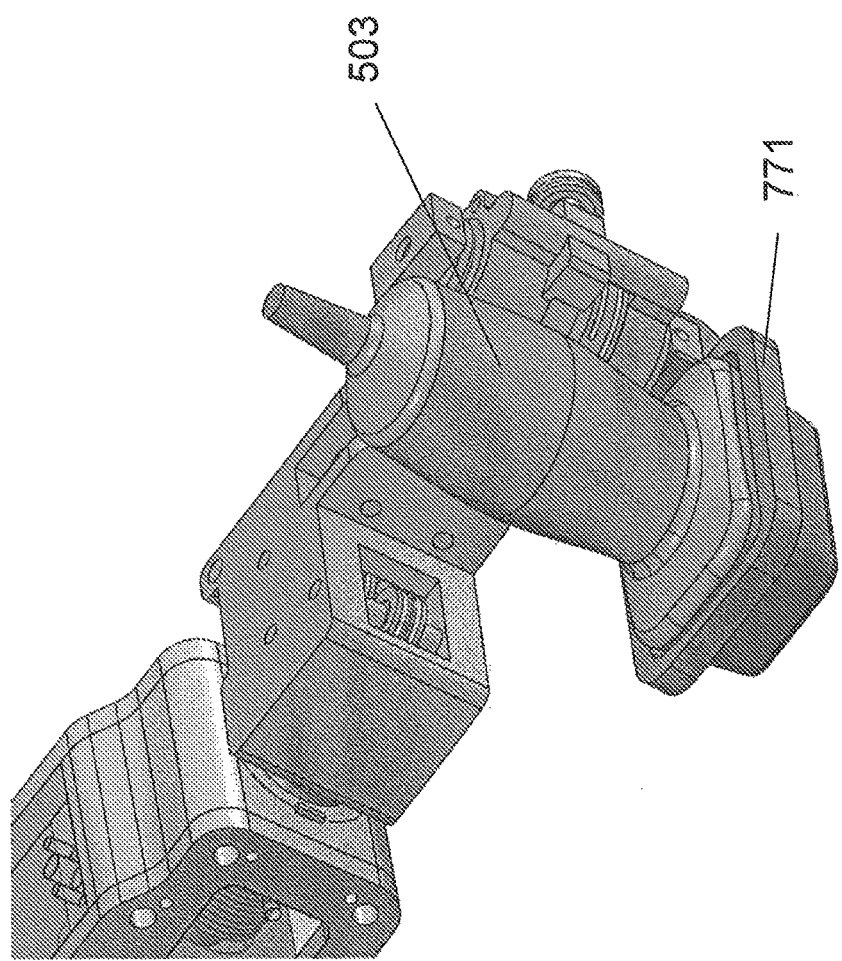
FIG. 7a shows an exemplary dummy transducer.

Further, referring to FIG. 7a, in some embodiments, a dummy transducer 503 consisting of non-metallic material can be used to place the same amount of pressure on the patient during radiation therapy as during treatment planning. The dummy transducer 503 can be shaped the same as or similar to a standard ultrasound transducer. The dummy probe can be configured to be snapped in and out of a holder 771 (see also FIG. 6a) on the manipulator 101. For example, the dummy probe can include a notch to facilitate repeatable snapping into the interface.

Figure 7B:
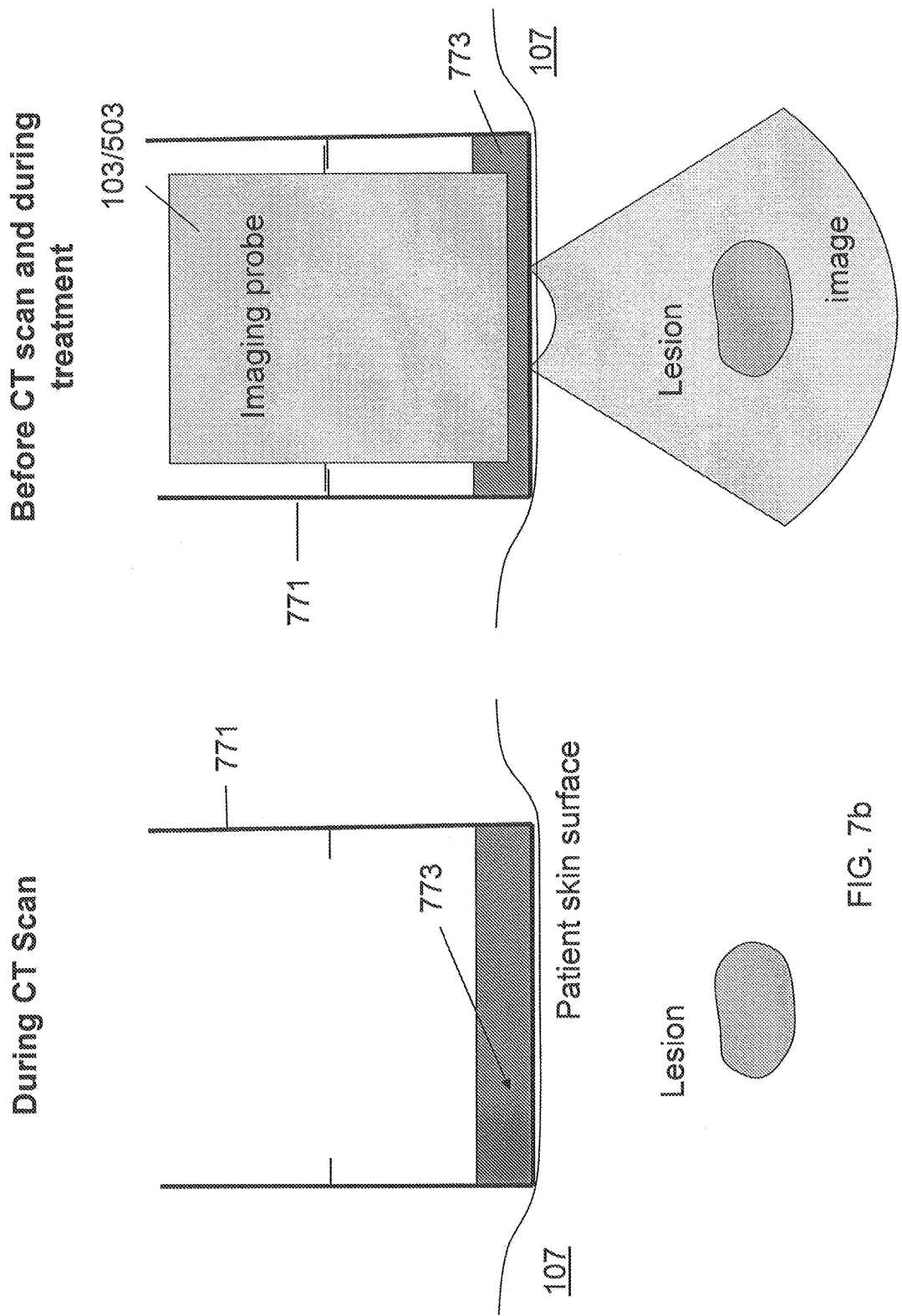
FIG. 7b shows a cup configured to hold a gel or fluid to hold the bottom of the transducer.

The connection between the manipulator and the probe can be configured to allow for snapping in and out of a real probe or a dummy probe. Referring to FIG. 7b, in some embodiments, the connection between the wrist 335 and the dummy transducer 503 (or probe 103) can include a cup 771 configured to hold a gel or fluid 773, and the bottom cup surface can be configured to contact the patient 107 during CT scanning. The imaging probe 103/503 can easily snap into and out of the cup 771 without actually touching the patient.

In some embodiments, even if materials are used that distort the image slightly, image processing techniques can be used to correct for the distortion.

Brakes

Figure 8:
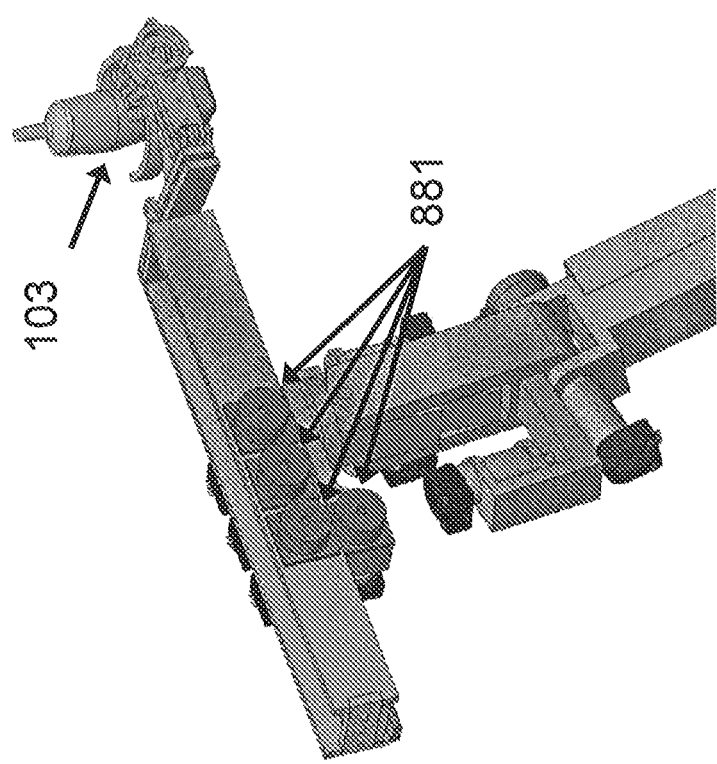
FIG. 8 shows brakes configured to control degrees of freedom of the manipulator.
Figure 9:
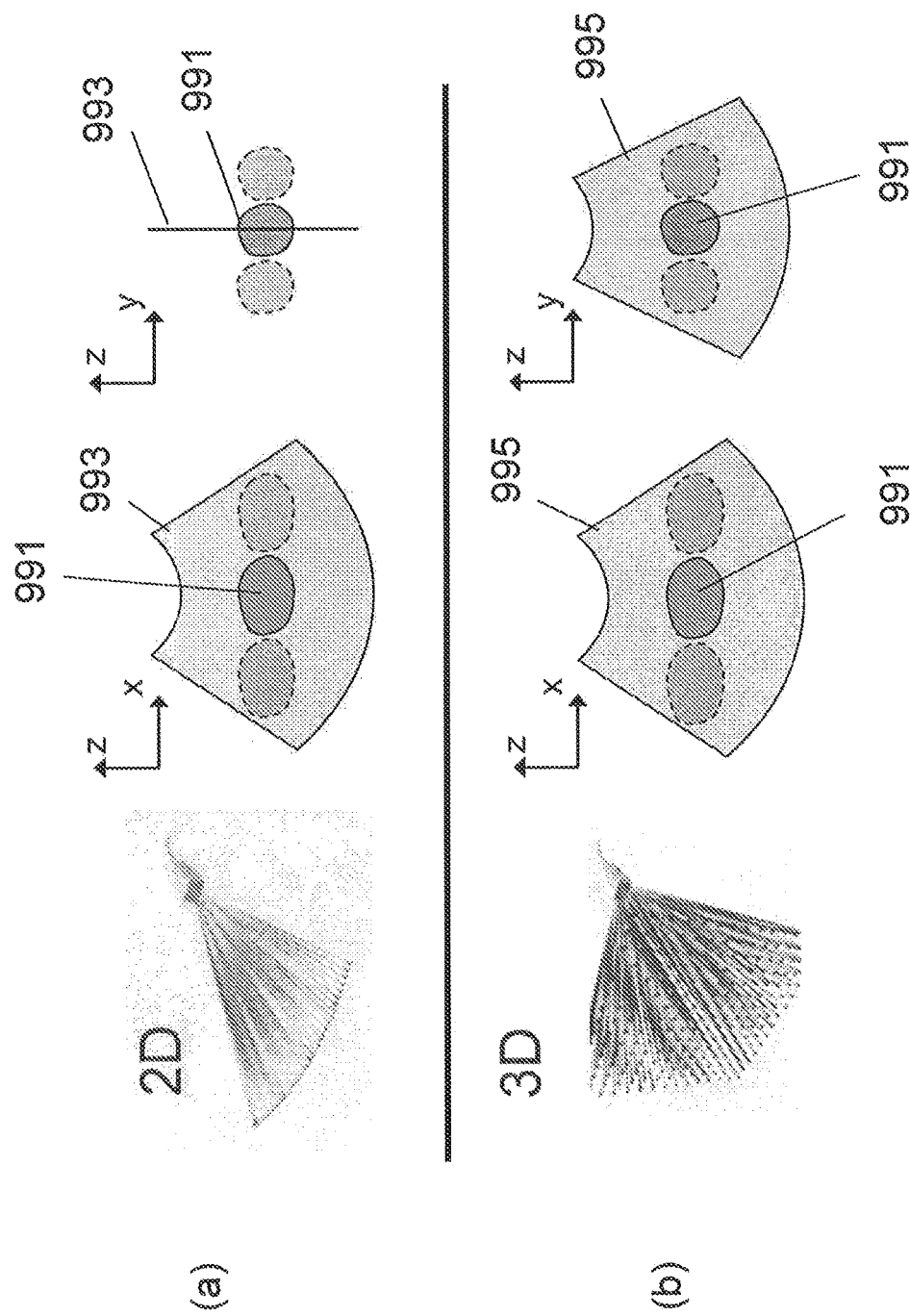
FIG. 9a shows movement of a target tissue relative to a 2D ultrasound sweep.
FIG. 9b shows movement of a target tissue relative to a 3D ultrasound sweep.

Another challenge associated with using an ultrasound imaging system during radiation beam therapy is positioning and maintaining the position of the ultrasound during treatment in the same location as was obtained during treatment planning. Accordingly, referring to FIG. 8, in one embodiment, brakes 881, such as electromagnetic, spring, or air brakes, can be used to control most, if not all, of the degrees of freedom of the manipulator 101. Using brakes 881 to control the degrees of freedom is possible because, rather than conducting a diagnostic scan where the ultrasound needs to be constantly moved, an ultrasound probe for use during radiation therapy typically maintains a fixed position during treatment, and small changes in the target position can be captured within the ultrasound image without requiring physical motion of the ultrasound transducer. That is, referring to FIG. 9a, a 2D ultrasound sweep 993 can capture the movement of a target tissue 991 in one plane (here, the xz plane), but not in a perpendicular plane (the yz plane) without moving the probe. In contrast, with a 3D ultrasound, the ultrasound sweep 995 can capture the movement of the target tissue 991 in both the xz planes and the yz planes without moving the probe. Thus, with 3D/4D ultrasound, a single transducer pose is able to capture small anatomy movements in all directions, thus alleviating the need for continuously adjusting the probe pose during beam delivery. Thus, the ultrasound system can have three or more degrees of freedom controlled by a brake and not a motor. Further, the probe manipulator can include very few motors to control additional degrees of freedom, such as only one motor.

In some embodiments, the probe can be configured to be free to move in the direction orthogonal to the patient to actively control probe pressure, but other axes can be locked using the brake system, significantly reducing system weight, size, and complexity.

Further, in some embodiments, referring to FIG. 10a-c, the brakes 881 can be configured to lock in place and/or have "memory," such as position sensors or encoders 883 configured to return the probe manipulator 101 to the desired position for imaging, making the ultrasound imaging more consistent from treatment planning mode to actual treatment. As a result, the therapist can place the ultrasound probe 103 in proper imaging position against the patient, then command the manipulator 101 to lock the probe's position using the brakes 881. This enables easy, precise, and repeatable probe placement against the patient before the treatment session, since the brakes can precisely lock in place according to the measured joint positions recorded during ultrasound imaging in treatment planning.

Brakes 881, such as electromagnetic brakes, have several advantages over traditional motors in the context of the workflow requirements of radiotherapy or other therapy. For example, the inertia of the brake rotors is much less than the inertia of typical motor rotors. Therefore, the reflected inertia of the spinning rotors felt by the ultrasound probe operator as they backdrive the manipulator to find the initial imaging position can be very low. Further, the overall weight of the brakes is far less than the weight of motors with comparable holding torque capabilities. This reduces the weight of the entire manipulator, making it easy for a therapist to mount and remove from the CT and treatment couches. An additional advantage of brakes is that they are passive devices, making them inherently safer than motors that are actively controlled during imaging.

In some embodiments, a motor can be used to control the medial-lateral motion of the manipulator to enable autonomous movement of the manipulator away from the treatment beam. This motor could also aid in temporal calibration of the system. The motor can be used in place of one of the brakes. Further, in some embodiments, the motor to control the medial-lateral motion of the manipulator can be the only motor used for the manipulator. In other embodiments, the motor can be one of two or three motors used with the manipulator.

Further, in some embodiments, a DC motor can be used to continuously control the probe's pitch during imaging to compensate for target motion. The motor can be used in place of one of the brakes (i.e., in place of the brake that controls the pitch). In some embodiments, the motor to control the pitch can be the only motor used for the manipulator. In other embodiments, the motor can be one of two or three motors used with the manipulator.

In use, a method of radiation therapy can include: (1) taking an ultrasound image of a patient's anatomy using an ultrasound system having an ultrasound transducer connected to a probe manipulator having a plurality of joints; (2) locking the joints of the probe manipulator in locked positions such that the transducer is in the desired location over the patient during the ultrasound; (3) storing the locked positions in a memory of the ultrasound system; (4) conducting a CT scan of a portion of a patient's anatomy; (5) removing the probe manipulator from the desired location before or after the CT scan; (6) returning the joints of the probe manipulator to the locked positions using the memory; and (7) conducing radiation therapy while imaging with the transducer while the transducer is in the desired position.

Series Elastic Force Controller

Figure 11:
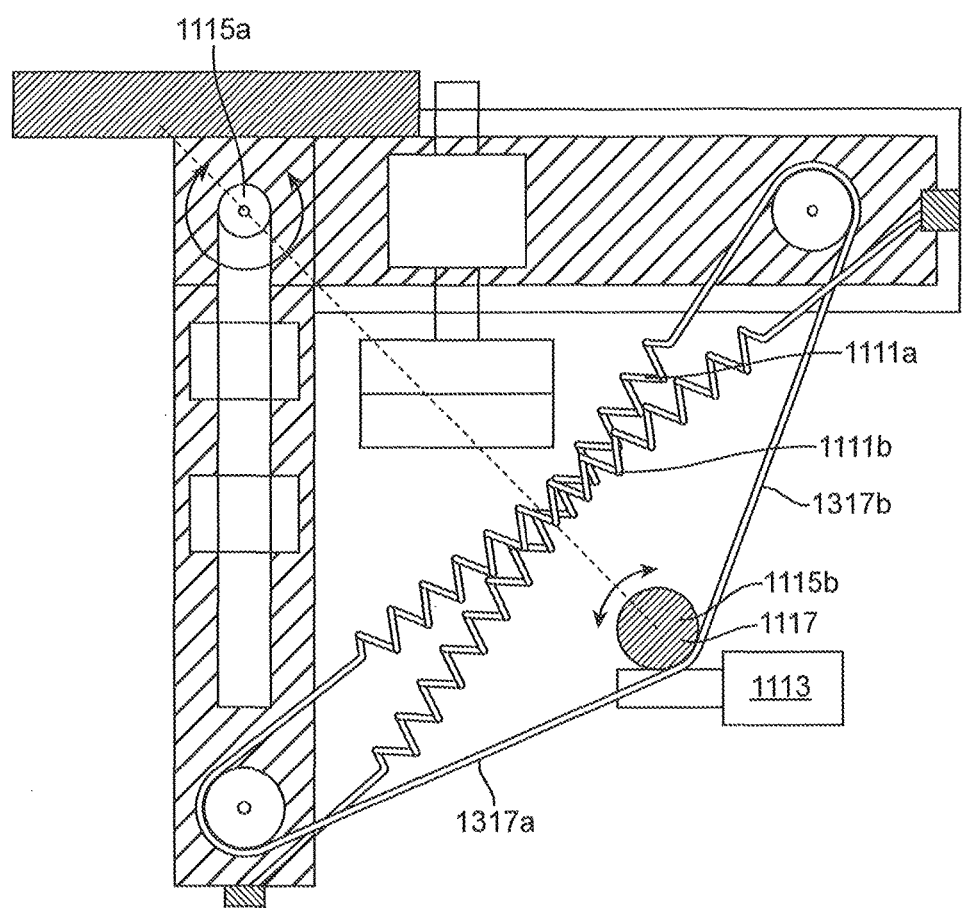
FIG. 11 shows a schematic of a series elastic force control on a probe manipulator.
Figure 12:
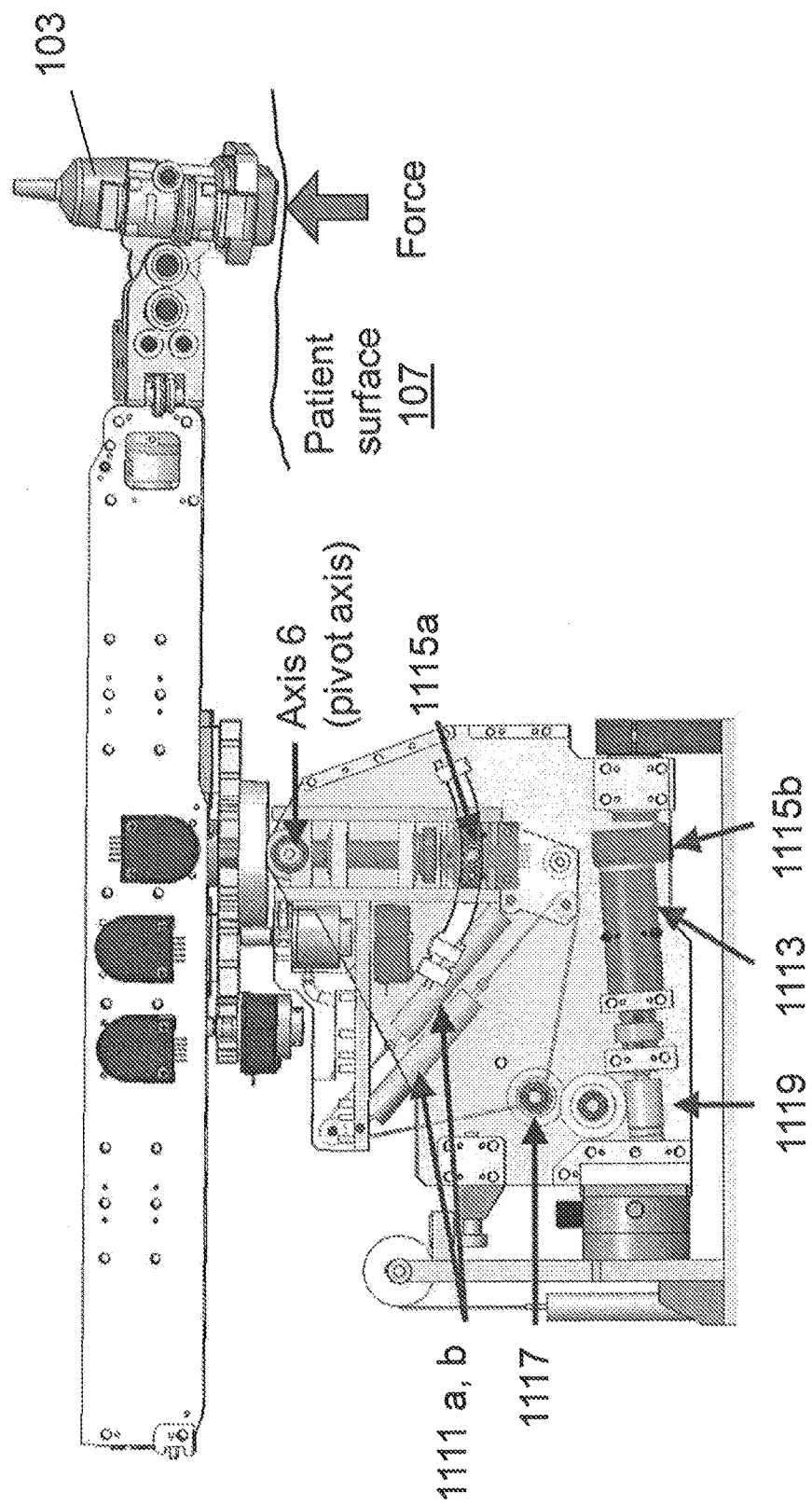
FIG. 12 shows a detailed view of a series elastic force control on a probe manipulator.

Another challenge associated with using an ultrasound system during radiation beam therapy is precisely controlling the amount of force placed on the patient while taking the ultrasound. Referring to FIGS. 11 and 12, in one embodiment, enhanced control can be introduced by using a series elastic spring control. Thus, the probe manipulator 101 can include at least one series-elastic actuator having a plurality of springs 1111a,b configured to control the amount of force placed upon a patient by the ultrasound transducer 103. In one system design (shown in FIG. 9), the series-elastic actuator can further include a motor 1113 to control the amount of elasticity of each of the springs. The motor can be connected to a capstan 1117 and one or more a position encoders 1115a,b. In some embodiments, the motor 1113 can be the only motor used for the manipulator. In other embodiments, the motor 1113 can be one of two or three motors used with the manipulator. In another system design, the series-elastic actuator can include a manual dial instead of a motor to control the amount of elasticity of each of the springs.

The position encoders 1115a,b can the amount of deflection of each of the springs 111a,b. That is, the encoder 1115a can be used to determine the configuration of the manipulator that allows placement of the manipulator in substantially the same position between treatment and planning. The other encoder 1115b can be used to determine the amount of force exerted on the patient. In some embodiments, a worm 1119 can be used to connect the motor 1113 to the capstan 1117. The worm 1119 can advantageously make the capstan 1117 non-backdriveable so that only a small motor 1113 is required to control the position of the capstan 1117, as described above.

The series-elastic transmission advantageously decouples the motor 1113 from the axis it controls (e.g., axis 6 in FIG. 12) and thus inherently increases human safety. It also enables force control of the ultrasound probe using two differential position encoders, thus alleviating the need for a physical force sensor, which could result in metal material close to the end effector. Other safety features can include using include a torque-limiting slip-clutch, software current limits, and joint limits for the manipulator.

Figure 13:
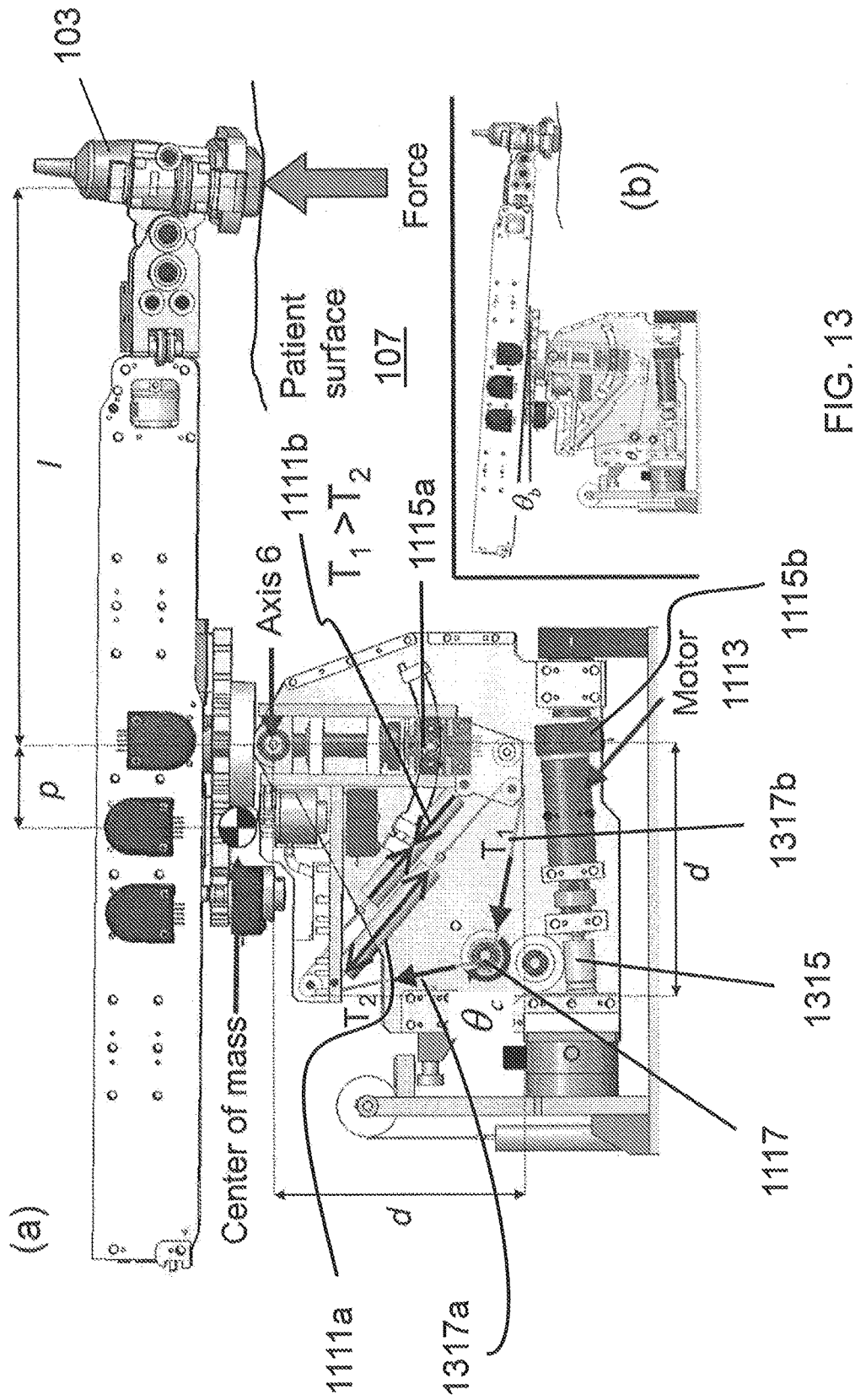
FIG. 13 shows use of a probe manipulator with a series elastic force control on a patient.

Referring to FIG. 13, one exemplary embodiment of a manipulator having series elastic transmission includes a motor 1113 and connected worm transmission 1315 configured to rotate the capstan 1317 clockwise. The rotation of the capstan 1317 causes the cables 1317a,b, which are connected to the ends of the springs and around the capstan (see also FIG. 11) to move in the indicated directions, causing more extension of spring 1111a and less extension of spring 1111b, resulting in a tension differential (T1>T2) between the cables 1317a,b coupled to the springs 1111a,b. This tension differential results in a change in the moments about axis 6, which controls the pivoting of the manipulator 101 towards and away from the surface of the patient 107 (pivoting towards the patient 107 causes an increase in the force exerted against the patient surface which pivoting away from the patient 107 causes a decrease in the force exerted against the patient 107). If the patient 107 remains stationary, the force exerted against the patient (F) is a function of the boom mass (m), capstan angle ($\theta_c$), boom angle ($\theta_b$), capstan radius (r), spring constants (k), and moment arms (l, d, p). Summing the moments about the freely-rotating axis 6 and assuming $\theta_b$ is small and slow moving:

$$\Sigma M_{A6} = 0 \approx F \cdot l + mg \cdot p + (T_2 - T_1) \cdot d \qquad \text{(Equation 1)}$$

where $(T_2 - T_1) \approx 2k \cdot (d\theta_b - r\theta_c)$

From Equation 1, the commanded capstan angle to achieve a given force F at a certain boom angle $\theta_b$ is $$\theta_c = \frac{F \cdot l + mg \cdot p + 2k \cdot d^2 \cdot \theta_b}{2k \cdot r \cdot d} \qquad \text{(Equation 2)}$$

The capstan angle $\theta_c$ is controlled using a closed-loop controller with the motor 1113 and encoder 1115b as the actuator and sensor. Since the patient's chest and abdomen are constantly expanding and compressing due to breathing, the boom angle $\theta_b$ is continuously changing, as is the commanded capstan angle to achieve force F according to Equation 2. Note that encoder 1115a in FIG. 13 is located in a circular slot far away from axis 6, yielding a high reduction ratio (such as greater than 20:1, e.g., 22:1) for encoder 1115a, and thus very high sensitivity for measuring $\theta_b$.

The capstan 1117 can be coupled to the motor 1113 with a non-backdriveable worm-gear transmission 1315. In one embodiment, the gear ratio of the worm-gear greater than 10:1, such as approximately 30:1. This particular transmission range advantageously (1) results in very little required motor current to move the capstan position; (2) allows the capstan position sensing resolution to be 30-fold larger than the native sensing resolution of encoder 1115b2; and (3) requires no motor current to keep the capstan fixed at a particular angle because the worm is not backdriveable. Note that although the worm 1315 is non-backdriveable, the series-elastic transmission itself is highly backdriveable because the springs 1111a,b decouple movements of the capstan 1117 from direct movements of the ultrasound probe 103. The springs 1111a,b can be selected have relatively long travel distances and relatively low spring constants, meaning that the probe 103 can be manually pushed away from the patient's skin easily in the event of a power failure or an emergency.

To prevent the spring system from providing resistance to the user during freehand probe placement before planning and treatment, the probe force F can be commanded to be zero. The capstan angle $\theta_c$ can be continuously adjusted during freehand probe manipulation according to Equation 2 achieve this objective.

Besides the inherent backdriveability and safety, the biggest advantage of the series elastic force controller is that it does not require a force sensor. When force sensors used in closed-loop force control systems, they often inject significant noise into the control loop, which can de-stabilize the system and pose a threat to the patient. Furthermore, force sensors are most effective when placed as close as possible to the force they are intended to measure in the system. Since force sensors contain metal, the sensor itself could cause CT artifacts and limit the available beam angles for treatment delivery when placed close to the ultrasound probe. In the series-elastic actuator, the two encoders measure deflection of the spring system, which yields an accurate model-based estimate of force without requiring a force sensor.

Redundant Degrees of Freedom

Another challenge associated with using an ultrasound system during radiation is providing access for the probe to a wide range of positions to accommodate a variety of physical obstacles, including LINAC placement, couch placement, and patients of various body shapes and sizes. In some embodiments, therefore, the ultrasound manipulator can include multiple degrees of freedom with at least one redundant degree of freedom. The redundant degrees of freedom can be proximal to the force control axis (described above) to allow the force control axis to be repositioned when the redundant degrees of freedom are moved.

Figure 14:
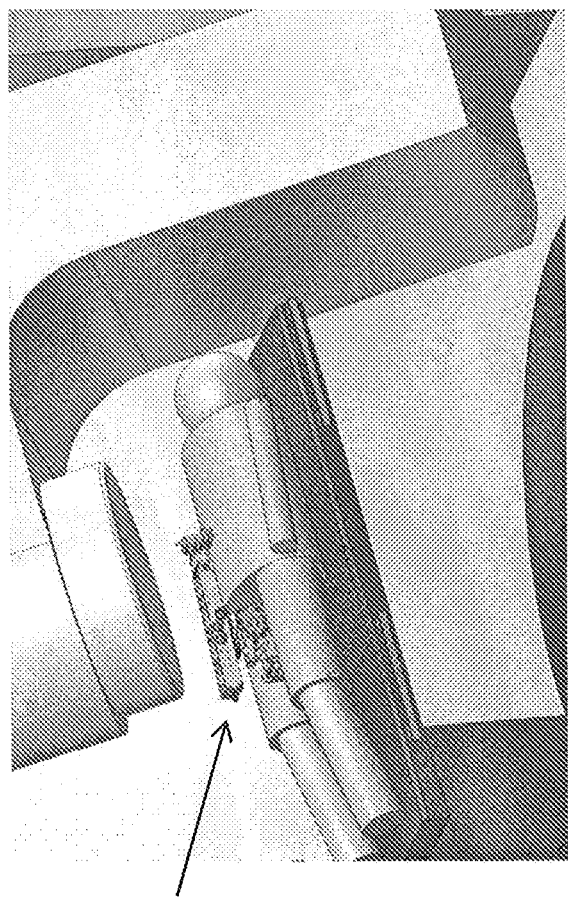
FIG. 14 shows placement of a probe manipulator relative to a patient.
Figure 15:
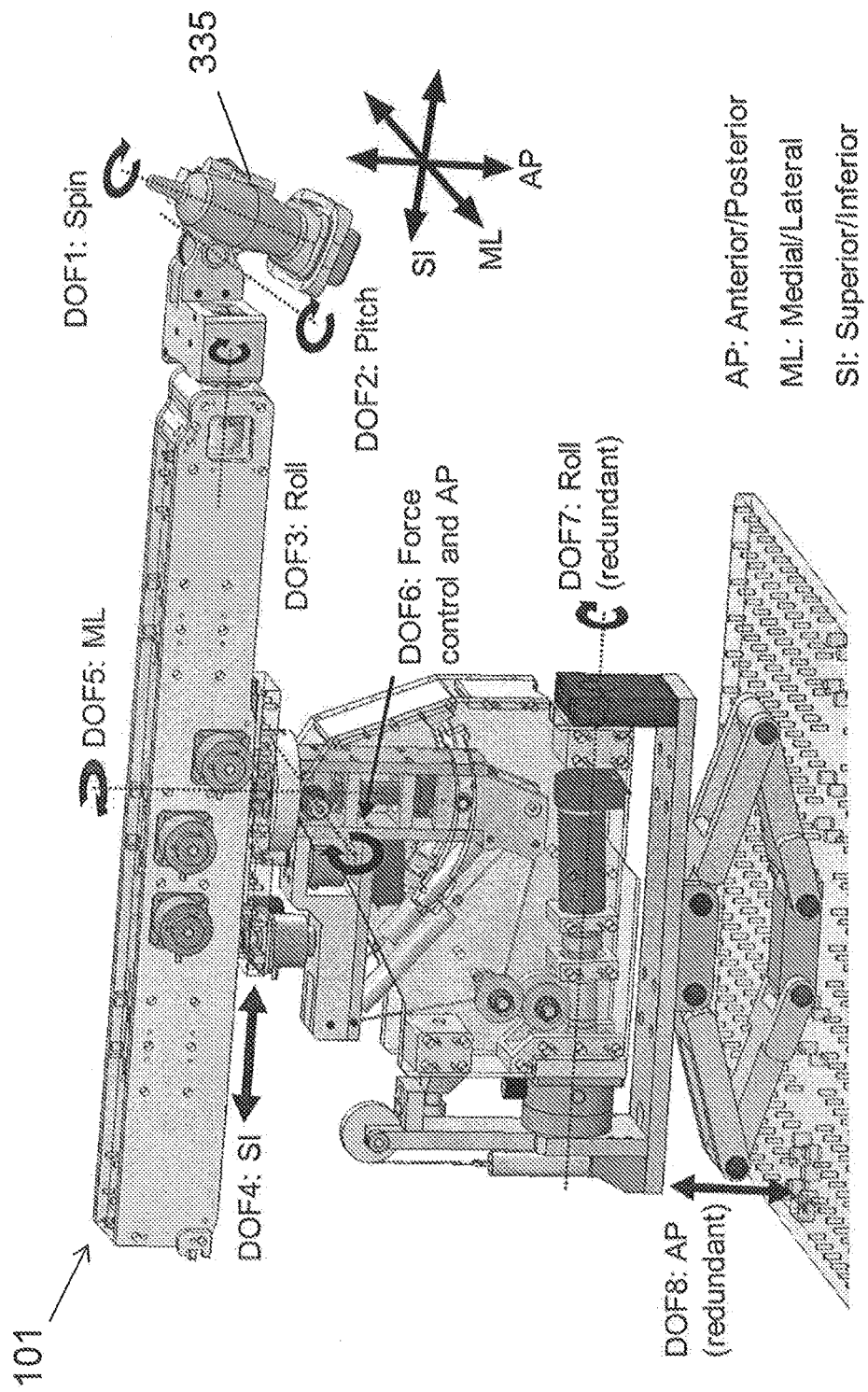
FIG. 15 shows degrees of freedom of a probe manipulator.

Referring to FIGS. 14 and 15, an exemplary probe manipulator 101 includes eight degrees of freedom (DOF). The 8-DOF manipulator kinematics are specified in FIG. 15. DOF 1 through 3 are rotational joints forming the plastic manipulator wrist 335 that primarily specifies probe orientation. DOF 4 through 5 specify the probe motion within the plane of the treatment couch (ML/SI plane). DOF 6 is a rotational joint coupled to a series-elastic transmission for controlling probe force. DOF 7 through 8 are redundant degrees of freedom to accommodate varying patient body sizes and varying imaging positions against the abdomen.

Figure 16:
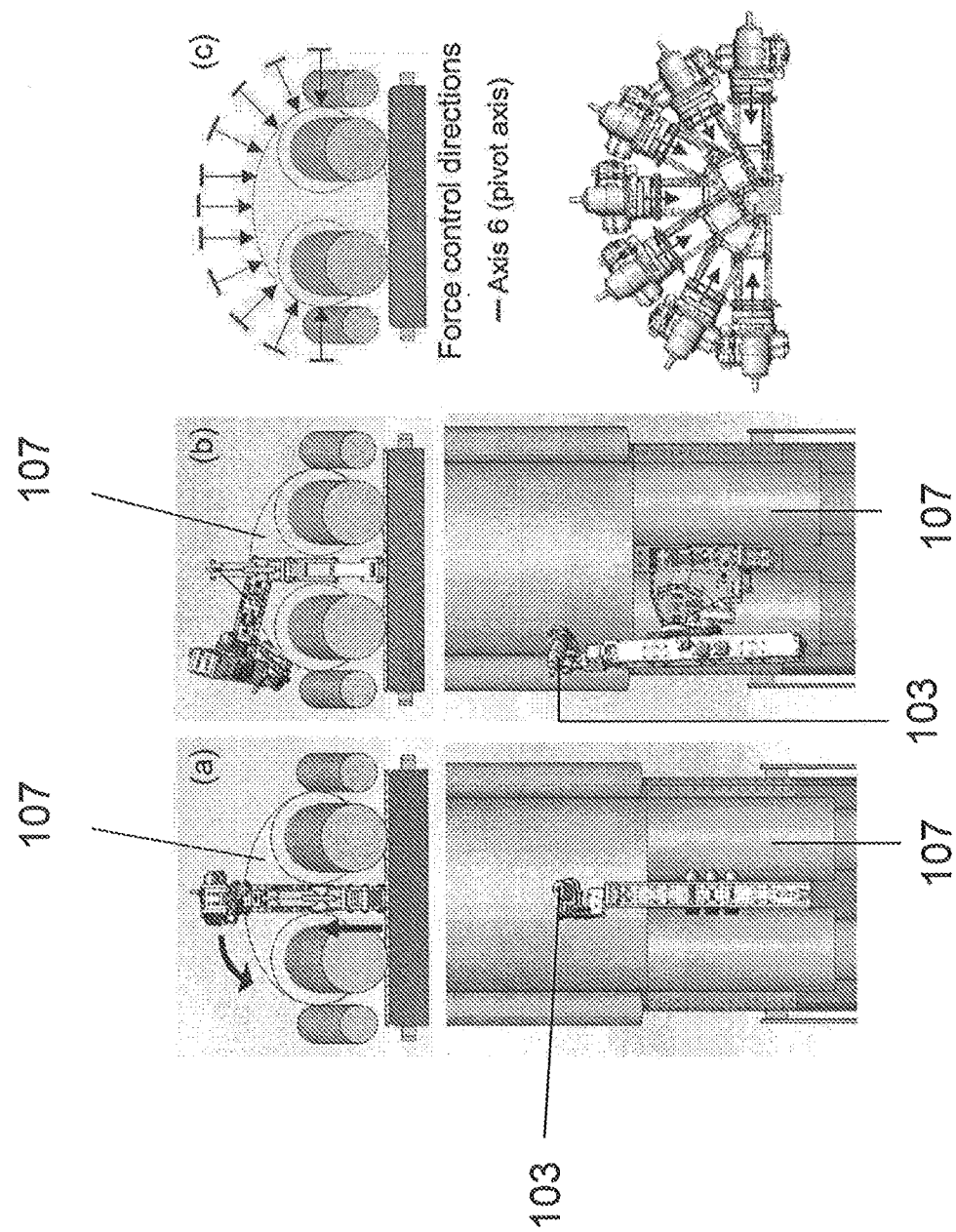
FIGS. 16a-16c show different positions of a probe manipulator having multiple degrees of freedom.
Figure 18G:
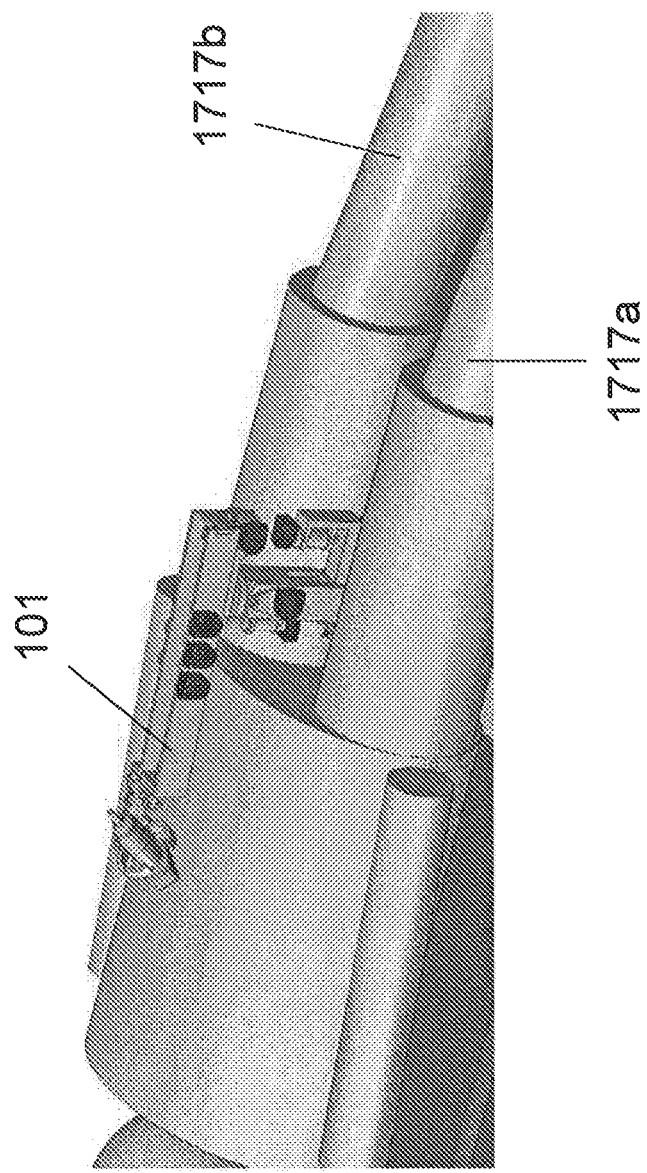

The redundant DOFs of the manipulator, DOF 7 and DOF 8, can provide flexibility for the manipulator to access a wide range of probe positions and patient body shapes/sizes. Referring, for example, to FIGS. 16a-16c, an adjustment of DOF 7 and/or DOF 8 can enable imaging with the probe 103 on the side of the patient 107, as is required to access liver lesions located underneath the ribs. A spring counter-balance system allows the manipulator to naturally rest in side imaging positions (see FIG. 16b) without needing to exert a large torque on axis 7 to keep the manipulator from falling. FIG. 16c depicts how redundant DOF 7 enables force control in the required directions. The series elastic force controller detailed in the section above provides fail-safe force control without requiring a force sensor, but is only capable of controlling forces in the direction orthogonal to axis 6. DOF 7 provides adjustment of the orientation of axis 6 relative to the patient, enabling the manipulator to press the probe in any desired direction in the axial plane shown in FIG. 16c.

Figure 34:
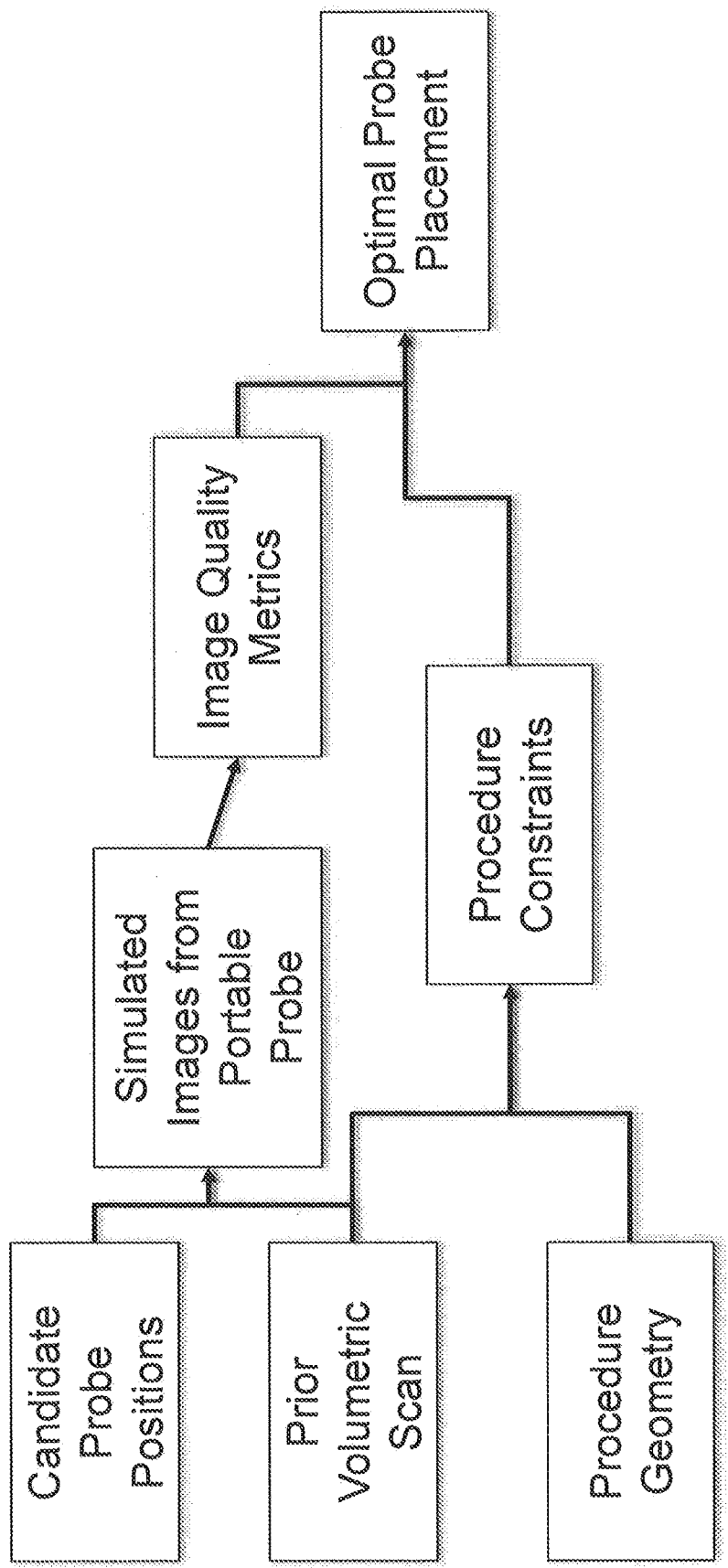
FIG. 34 is a flow chart for choosing a probe position.

Referring to FIG. 34, the ideal positioning of a portable imaging probe against a patient for purposes of guiding a medical therapy can be determined. The method enables the probe operator to find good quality probe position (one that yields high quality images) without having to exhaustively scan the probe across the patient's abdomen. The method also enables the probe operator to place the probe such that it does not interfere with the planned therapy. Images from the portable probe can be simulated on a computer from a wide range of candidate probe positions on the patient's abdomen. Probe positions that contain the therapy target and/or important surrounding anatomy are considered. The images can be simulated using properties of a prior medical imaging scan of the patient (CT, MRI, PET, etc.) and geometrical knowledge of the candidate probe portions and orientations. The simulated images can be evaluated based on quality metrics derived from image processing. In the case of ultrasound imaging, metrics can include the presence of bowel gas or bone in the images, since these cause shadows in ultrasound images that negatively impact image quality. Quality metrics can also include the appearance of target anatomy and surrounding structures. In parallel, knowledge of the medical procedure geometry is used to produce a second set of constraints relating to the procedure. For example, in radiotherapy, geometrical constraints could give preference to probe placements that lay outside the prospective path of the radiation beam. Procedure constrains can also incorporate the geometry of any manipulators or entities holding the ultrasound probe in place during the procedure. For example, in real-time radiotherapy guidance, preference can be given to probe and manipulator configurations that avoid physical collisions with the LINAC and also beam interferences. In catheter procedures, preference can be given to probe and/or manipulator placements that avoid occluding fluoroscopic x-ray images taken during the procedure. In biopsy, probe placements that avoid the best path of the needle towards the target can be given preferential weighting. Image quality and procedure metrics are combined into a weighted score that rates various probe placement candidates, and selects those probe placements(s) that are most optimal (ideal) for the particular patient and procedure. A visualization platform and/or a probe manipulator can help guide the probe operator towards the optimal probe placement(s) selected by the method.

Mounting Points

Another challenge associated with using an ultrasound system during radiation beam therapy is finding an appropriate place to mount the probe manipulator and associated mechanical parts. Candidates for mounting the manipulator include the floor of the LINAC room, on the ultrasound machine cart, the side of the couch, a fixture above the couch, and between the patient's legs.

In one embodiment, as shown in FIG. 17, the manipulator 101 is mounted between the patient's legs 1717a,b, which results in a very compact and lightweight design that is easy for the therapist to maneuver and manage, and relatively comfortable for the patient. Various imaging positions for the probe when mounted between the patient's legs 1717a,b are shown in FIGS. 18a-18g.

Figure 19:
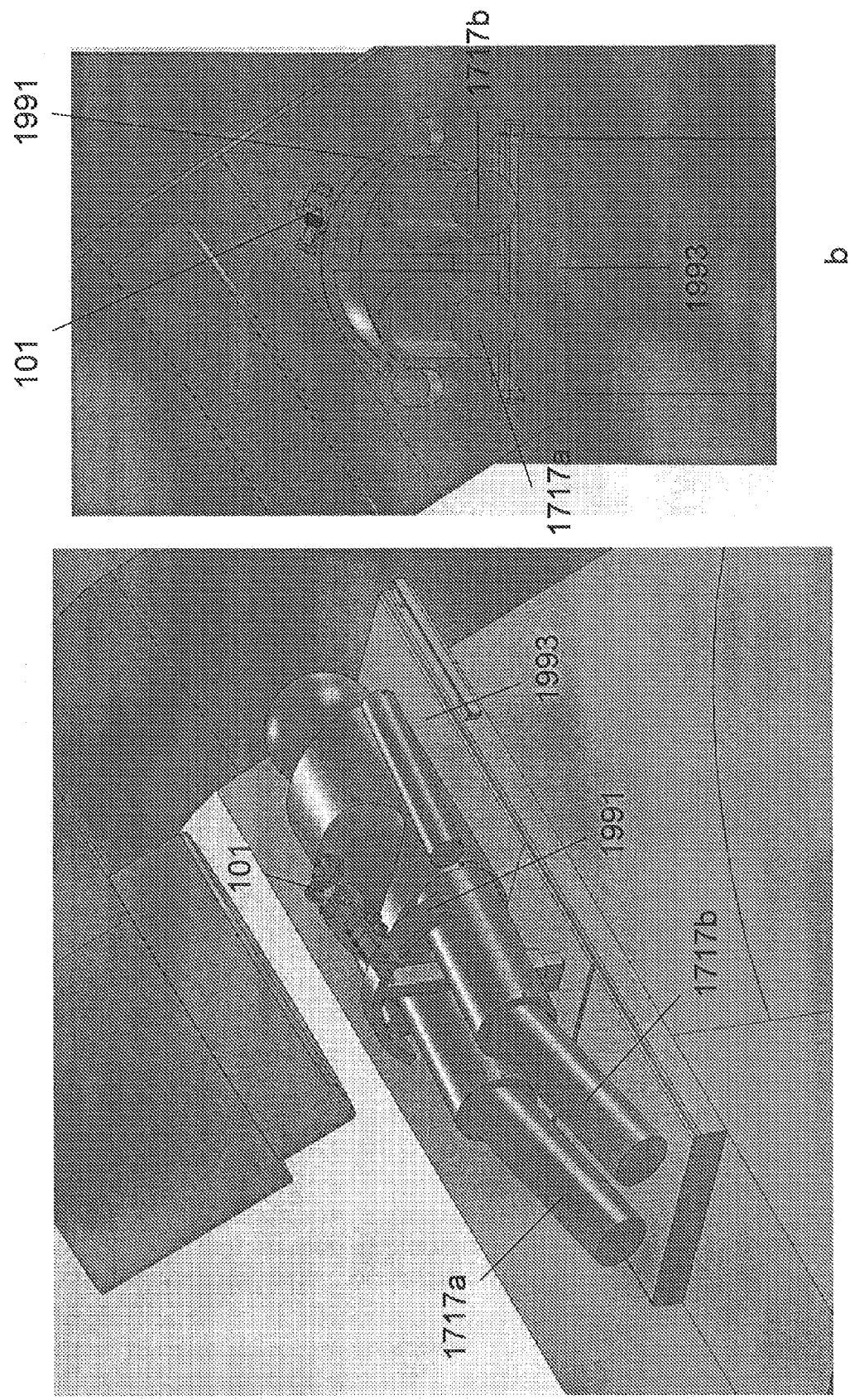
FIG. 19 shows a probe manipulator mounted to rails rather than between a patient's legs.

In another embodiment, shown in FIG. 19, the manipulator 101 can be mounted to rails 1991 attached to the treatment couch 1993 rather than mounted directly between the patient's legs 1717a,b.

Figure 20:
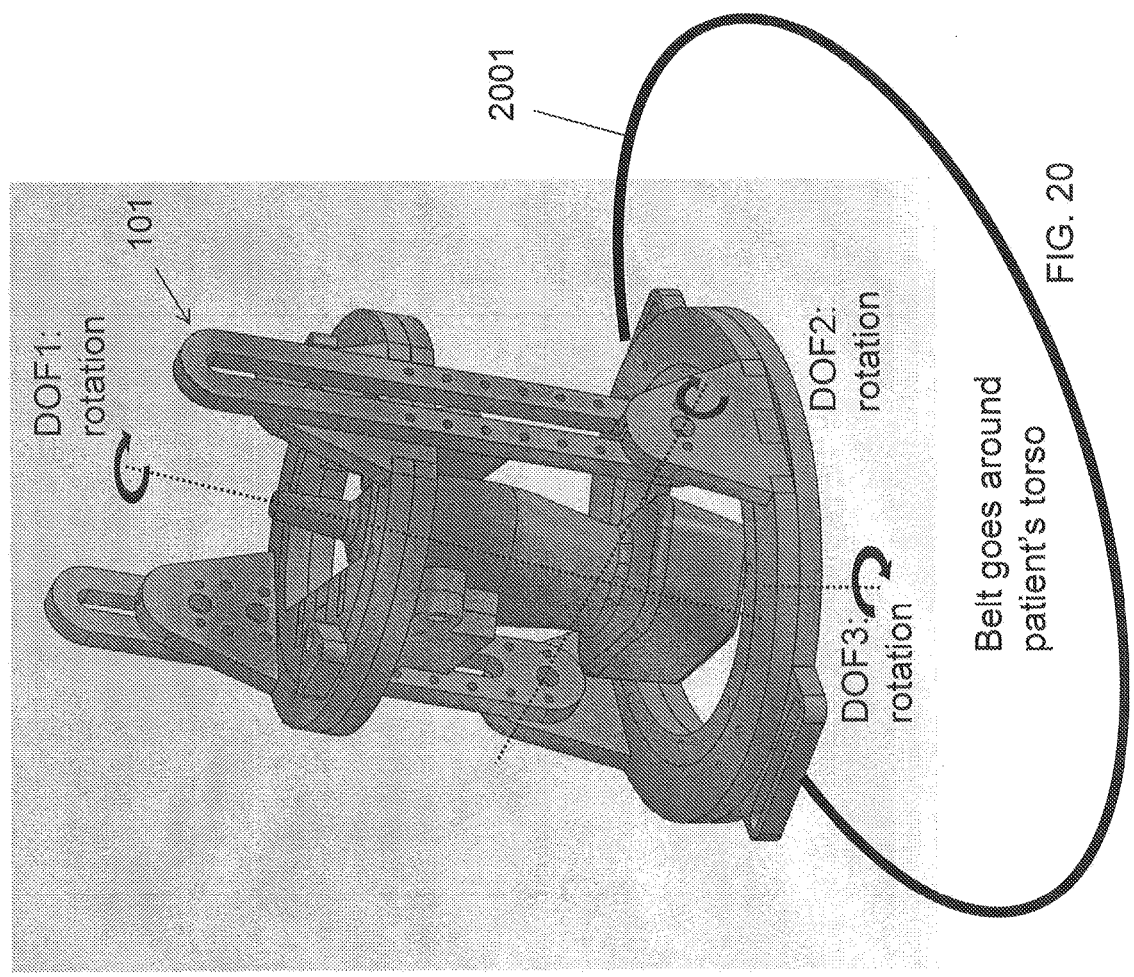
FIG. 20 shows a manipulator place on a patient's abdomen with a belt looped around the patient's torso.

In another embodiment, referring to FIG. 20, the manipulator 101 can be placed directly on a patient's abdomen and a belt 2001 can loop around the patient's torso to hold the manipulator 101 in place.

Calibration

Another challenge associated with using an ultrasound system during radiation beam therapy is ensuring that the portable imaging probe is properly calibrated. Part of that calibration can require the synchronization of the probe image stream and the spatial tracker that is mounted to the probe (for example, optical tracking markers, electromagnetic tracker, or mechanical tracker).

In some embodiments, the relative time difference between the tracking data and image data can be quantified by utilizing the precise positioning capabilities of the probe manipulator. The temporal calibration method involves: (1) setting up an imaging phantom that contains at least one high-contrast, easily localizable target and fixing an external tracking device to the probe; (2) gripping the probe in the manipulator holder and placing the probe against the phantom such that moving one axis of the manipulator causes movement of the target within the probe image and tracking the target in the raw image using image processing (for example, normalized cross correlation); (3) commanding the manipulator to pitch the probe in a sinusoidal motion pattern at a set frequency, such as 0.2 Hz, and recording the location of the target as a function of time over several pitch cycles as well as the position of the tracking sensor; (4) fitting a sine wave of frequency f to each data set, comparing the phase difference of the two sine waves to find the relative time difference. In one embodiment, the phase difference between the optical tracking and US systems is 80-100 ms, such as 89 ms.

In one embodiment, the probe manipulator can be used for enhanced ultrasound calibration. Thus, the probe manipulator can be used to lock certain degrees of freedom during the spatial calibration process, thus making it easier to isolate certain directions of probe movement during spatial calibration, which could speed the process as well as ensure a better calibration. Furthermore, the manipulator can assist temporal calibration by moving in a precise sinusoidal manner, as described above.

Tissue Tracking

Another challenge associated with using an ultrasound system during radiation beam therapy is closely tracking the target to ensure that the radiation beam is delivered precisely as planned. To solve this problem, real-time ultrasound images acquired during beam delivery can be compared with ultrasound/CT images collected during treatment simulation or planning.

Figure 21:
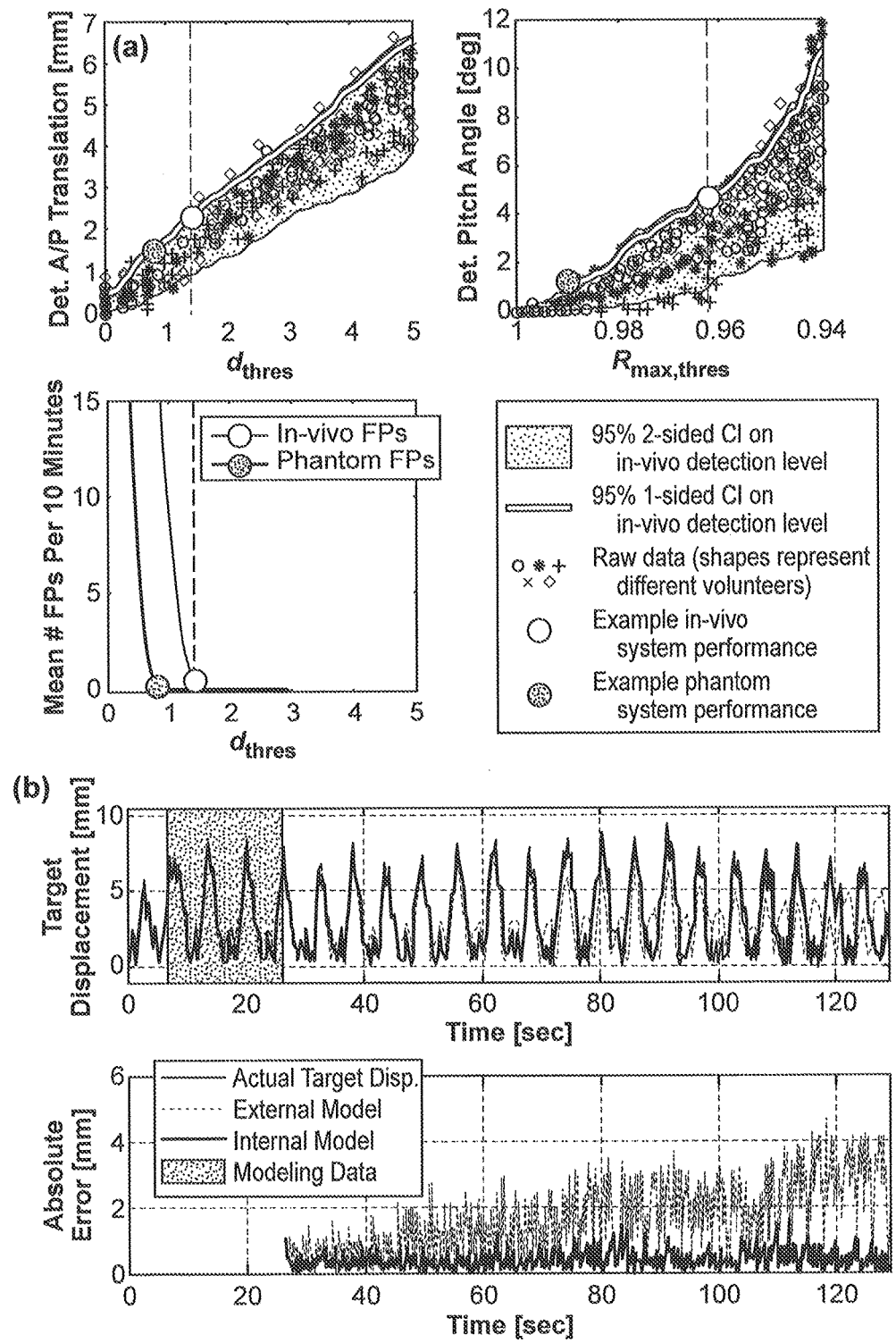
FIGS. 21a-21b shows in-vivo template-based planar target monitoring.

Referring to FIG. 21, in one embodiment, 3D target tracking can be performed in multiple 2D ultrasound imaging planes, such as orthogonal 2D planes. Thus, the system can track planar displacements and rotation simultaneously in two orthogonal imaging planes. Tracking information from multiple planes can be fed through a probabilistic Kalman filter that estimates the target's position based on geometric relationships between the planes and the transducer's spatial resolution (sensing uncertainty) in each direction. The software can thus: (1) obtain a first series of 2D images of a target in a first plane using an ultrasound transducer; (2) simultaneously with obtaining a first series, obtain a second series of 2D images of the target in a second plane that is orthogonal to the first plane using the ultrasound transducer; and (3) estimate the position of the target based upon a geometric relationship between the planes and a spatial resolution of the ultrasound transducer. This system can advantageously allow the determination of movement of the tissue in three directions while avoiding the computational intensity and time lags of volumetric tissue tracking.

Using a low-resolution 2D US probe and two image-based parameters derived from template tracking methods, in-plane prostate displacements and rotations can be detected in-vivo before exceeding 2.5 mm and 5° at 95% confidence with processing times under 16 ms (FIG. 21a). Further, tracking liver features with ultrasound can be significantly more accurate than relying on signals from an external surrogate marker (FIG. 21b). In some embodiments, the template-based target monitoring method can be extended to 3D by tracking planar displacements and rotation simultaneously in 2 orthogonal imaging planes as enabled by multi-planar transducer imaging modes. Tracking information from multiple planes can be fed through a simple probabilistic filter that estimates the target's degree of freedom pose based on geometric relationships between the planes and the transducer's spatial resolution (sensing uncertainty) in each direction. A rotated 2D template can be used matches the ultrasound image for angular tracking purposes.

In another embodiment, referring to FIG. 22, volumetric processing of dense 3D US data can be used to produce highly accurate patient-specific motion estimates. Three dimensional intramodality image registration can be implemented using mutual information (MI) or other methods. The software can include rapid patient-specific modification of parameters such as median filtering kernel size, number of intensity quantization bits, interpolation algorithm, and region of interest size. Each of these variables eliminates potentially useful information from the data in order to facilitate faster processing and the removal of local maxima/minima caused by speckle noise in the MI function to be maximized. The software can thus balance the tradeoff between information loss (resulting in decreased registration accuracy), optimization robustness, and optimization speed for each target organ. Note that feature-based methods such as attribute vector matching can also be used for patient-specific volumetric target tracking. The methods can be strictly rigid or include deformable registration.

A 3D intramodality image registration using mutual information (MI) can thus be implemented. FIG. 22 shows results for 3 pairs of 3D prostate registrations using MI. Upon introducing simulated displacements on 3D US data before MI registration, the magnitude of the computed displacement error was smaller than 2.25 mm in 95% of the cases and smaller than 1.25 mm in 90% of the cases (FIG. 22a).

In another embodiment, a hybrid system can be implemented which combines multi-planar and volumetric target tracking to capitalize on the high bandwidth of multi-planar tracking and the high accuracy of volumetric registration. A full 3D ultrasound volume can be collected and registered to a reference volume at adjustable time intervals, depending on registration speed and target motion. Between acquisitions of full ultrasound volumes, the transducer can be switched to multi-planar imaging mode and targets will be tracked at high-bandwidth as described above. A Kalman filter can continuously integrate tracking information from both tracking modes into a motion model in order to estimate target pose with optimal accuracy and speed based on each mode's capabilities.

In another embodiment, a visualization and manual tracking system can include overlays of the 3D ultrasound anatomy and the radiation treatment plan such that a human operator can manually assert an intervention signal to the LINAC whenever they visualize the target moving out of the planned dose distribution.

In some embodiments, a dynamic approach can be used in which the current imaging plane locations are continuously adjusted within the 3D imaging volume such that feature cross sections appear similar between image frames. In other embodiments, a feature-based approach (both rigid and deformable) for volumetric target tracking, such as attribute vector matching, can be implemented.

Treatment Planning Techniques

Another challenge associated with using an ultrasound system during radiation beam therapy is implementing mechanisms for avoiding interference of radiation by the probe manipulator, the ultrasound transducer, patient movement, and/or the patient couch. If the radiation hits or runs through any of these obstacles, then the original radiation treatment plan will not be able to be carried out effectively, as the obstacles, such as the image guidance hardware, can absorb part of the radiation dose and thus change the dose distribution delivered at the time of treatment.

Figure 23:
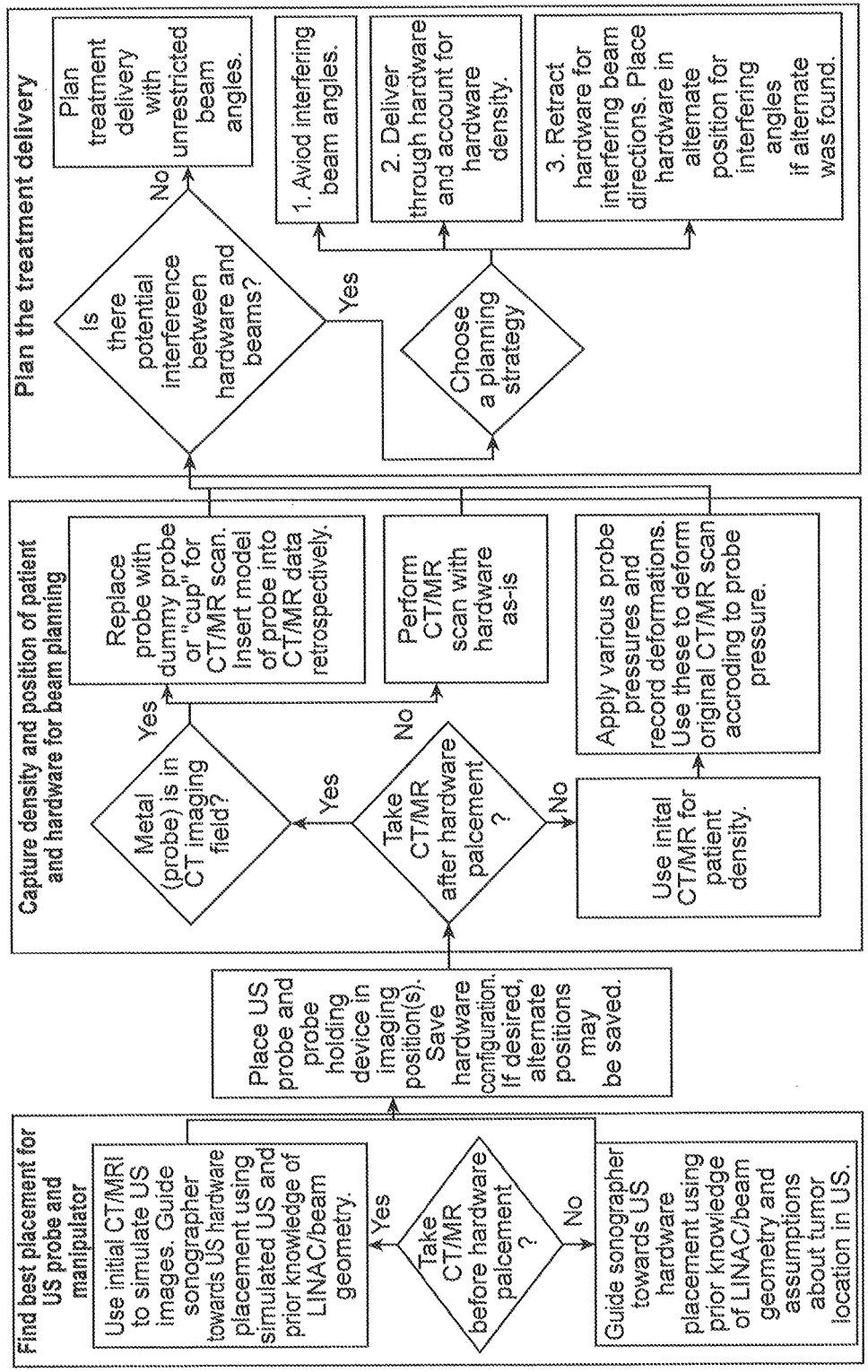
FIG. 23 is a flow chart for radiation treatment planning using an ultrasound and manipulator.

Referring to FIG. 23, treatment planning can involve finding the best placement for the ultrasound probe and manipulator, placing the probe and manipulator in the desired location, capturing the density and position of the ultrasound probe and the patient, taking a CT image, and planning treatment and delivery (which can involve avoiding interfering beam angles, delivering through hardware and accounting for hardware density, or retracting hardware for interfering beam directions).

Avoiding Collision or Interference Between Manipulator/Probe and Radiation Beams Referring to FIG. 24a, in one embodiment, the radiation beam 2525 from the LINAC 105 that interfere with the probe manipulator 101 and/or the probe transducer 103 are avoided (as opposed to implementing a radiation beam 2525 that goes through or into the manipulator 101 or probe 103 as shown in FIG. 24b). A 3D software application can be implemented that enables patient-specific visualization of the ultrasound probe manipulator, ultrasound probe, treatment setup (LINAC and treatment couch), and patient model derived from planning CT data. The ultrasound probe placement and manipulator position used to image target sites, such as abdominal sites, of the patients can be saved using the manipulator's joint encoders and utilized to precisely place the image guidance hardware within the virtual environment. Radiation beams can be projected outward in 3D from the LINAC head for each potential LINAC gantry angle. Ray-based or bounding-geometry-based collision detection methods are implemented to detect geometric interference between the projected radiation beams and the image guidance hardware models. Interfering beams are avoided during the treatment planning process. Furthermore, potential collisions between the probe manipulator, linear accelerator, and treatment couch can be visualized in advance and avoided using the software. The software can further inform and investigate different positions, configurations, or placements of the probe manipulator relative to the patient such that the manipulator does not interfere with critical radiation beams in the treatment planning process.

Thus, in one embodiment, there can be a software environment that contains the manipulator, ultrasound transducer, radiation beams, linear accelerator, and patient CT model. The interference between the radiation beams and the manipulator/US probe in 3D can be visualized or in a set of orthogonal planes in the software and/or the interference can be automatically detected using existing ray-based or bounding-geometry-based collision detection algorithms. The position of the manipulator within the software environment can be determined based on image segmentation of the manipulator links in the CT scan and/or saved joint position information for the manipulator during the planning stage. The position of the ultrasound probe in the software is determined via 3D tracking, manipulator joint info, or segmentation. In some aspects, only avoid certain parts of the manipulator and/or ultrasound probe are avoided in the planning. For example, if one part of the ultrasound probe is metal and the rest is plastic, the software can avoid only the metal while allowing delivery of radiation through the plastic part as well as through the manipulator.

During treatment planning, the number of beams, beam angles, shapes, and intensities to be used during radiotherapy treatment can be selected in order to achieve a particular absorbed dose distribution inside the patient. Treatment planning typically involves the collection of a computed tomography (CT) scan that can be used in conjunction with the planned beams to estimate the absorbed dose. Ultrasound images can be taken before, after, or during the CT scan. The closer the ultrasound image is taken to the actual time of the CT scan, the less chance the patient's anatomy has moved between CT and ultrasound, and the more reliably the patient can later be placed in treatment position based solely on ultrasound images.

Figure 25:
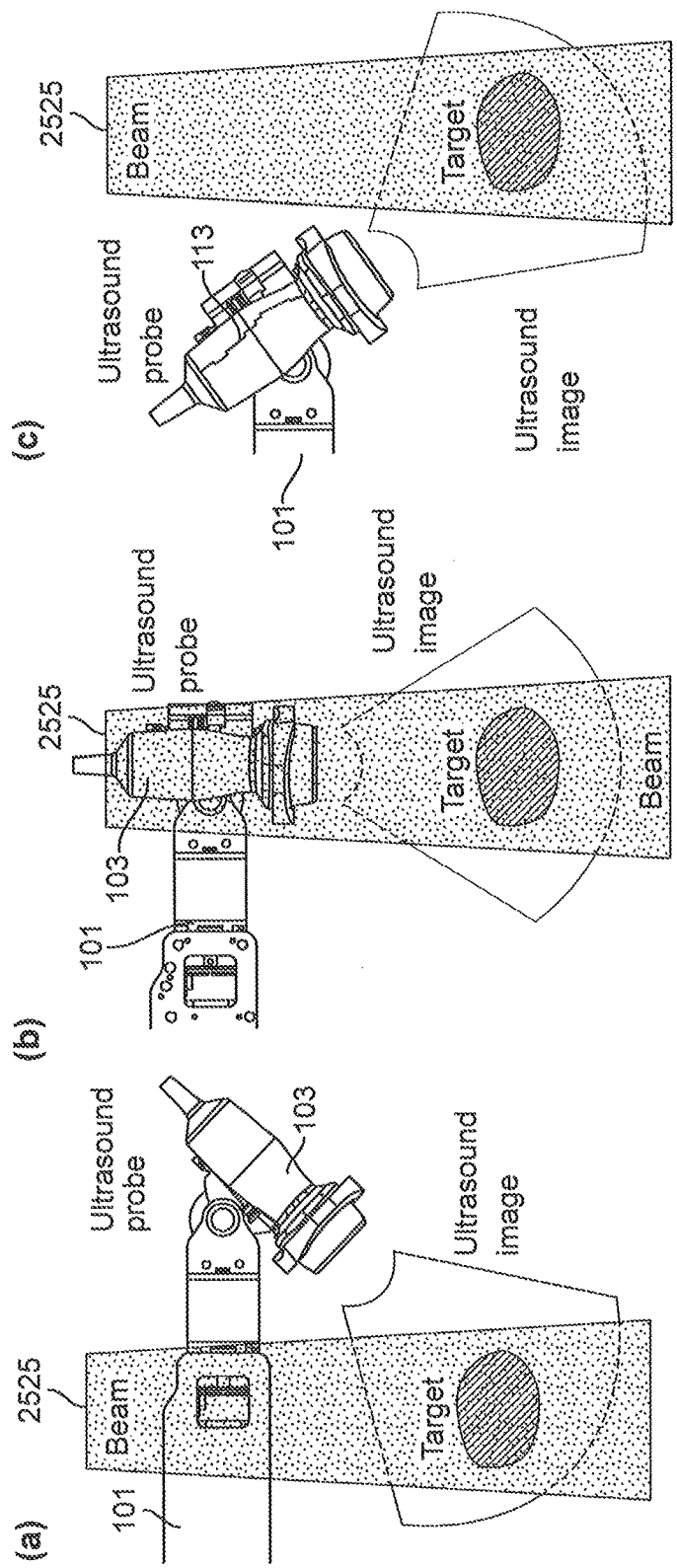
FIGS. 25a-c show various positions of an ultrasound probe relative to radiation beams.

In some embodiments, the initial placement of the manipulator and ultrasound probe can be selected so as to avoid positions where the highest likelihood for beam interference will occur. Referring to FIGS. 25a-c, the position of the ultrasound probe 103 shown in FIG. 25c is the most favorable position, since the anterior radiation beam 2525 does not interfere with the ultrasound probe or the manipulator. In this case, the LINAC can rotate 360 degrees around the patient, and no radiation 2525 beam will pass through the image guidance hardware. In addition, a CT scan can be performed concurrently with ultrasound imaging, since no metal is present in the CT field. If the position shown in FIG. 25c is not possible due to bowel gas, rib, or other ultrasound image obstructions, the position shown in FIG. 25a is the next best. In this position, the beam passes through the manipulator 101, but not through the ultrasound probe 103. In this case, CT can still be performed concurrently with ultrasound imaging since the distal end of the manipulator is constructed out of plastic material that will not cause CT artifacts. However, the presence of the manipulator must be taken into account when planning the radiation beams, since the plastic manipulator will absorb a certain amount of radiation dose. If neither the positions shown in FIG. 25a or 25c is available for imaging, the position shown in FIG. 25b can be used. This can be the least favorable position, since both the manipulator and ultrasound probe interfere with treatment beams and must be accounted for in the treatment planning (which is much harder to do with the metal of the ultrasound probe). In addition, CT generally cannot be performed concurrently with ultrasound imaging due to probe artifacts in the CT scan.

Figure 26:
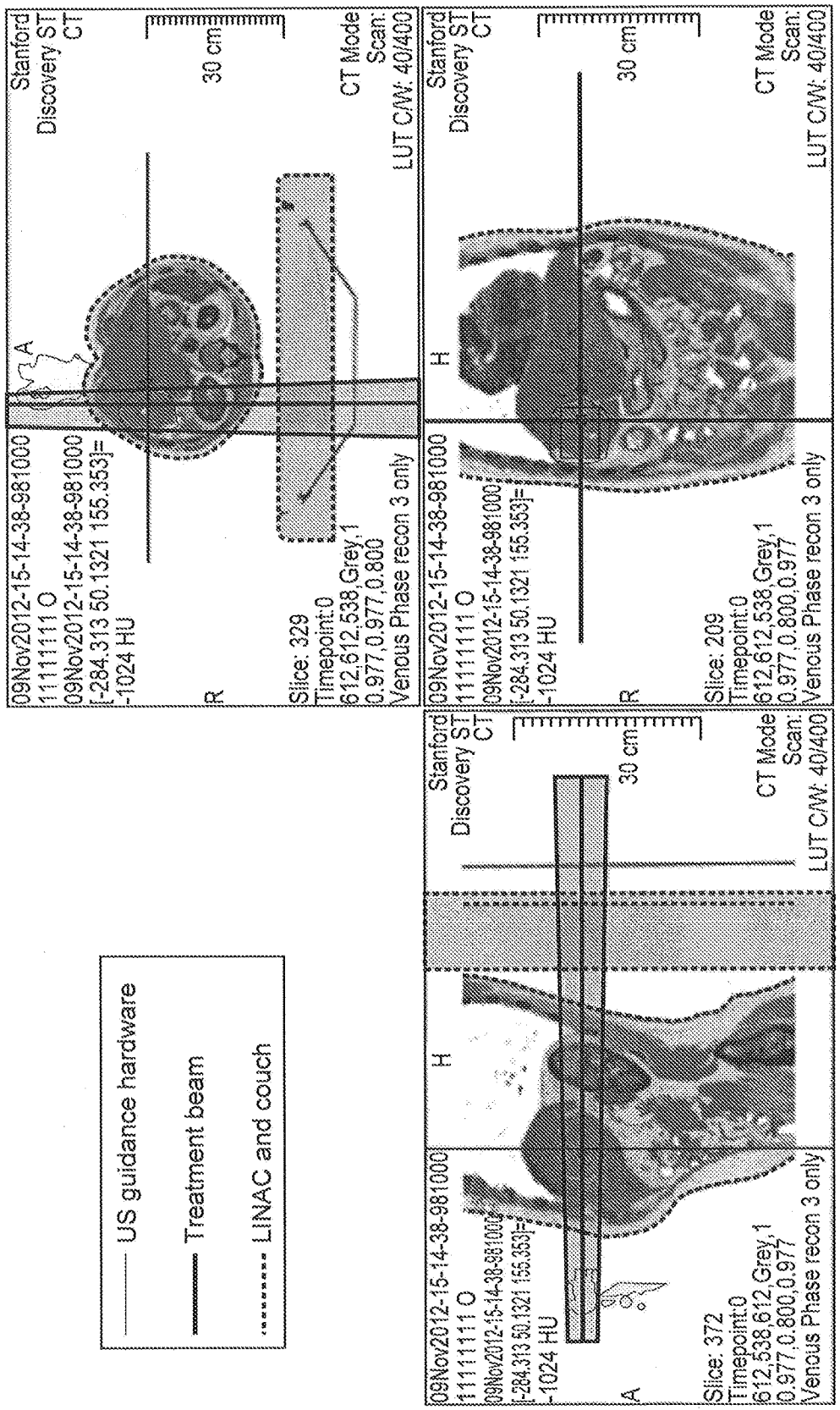
FIG. 26 shows a visualization platform where the probe, probe manipulator, LINAC, and beam are seen.

FIG. 26 shows an illustration of the visualization platform where the probe, probe manipulator, LINAC, and beam are seen. Intersections between these entities are easily visualized and can be avoided as part of the treatment planning process. Thus, referring to FIG. 26, in some embodiments, during initial placement of the ultrasound manipulator and probe, potentially interfering hardware positions can be predicted using a software program that enables 2D and 3D visualization of the LINAC, couch, treatment beams, manipulator, ultrasound probe, and patient. The prospective locations of treatment beams can be used by the software based on the position of the tumor as identified in the spatially localized ultrasound images as they are collected in real-time identified based on previous CT, magnetic resonance imaging (MRI), ultrasound, or positron emission tomography (PET) images acquired of the patient prior to treatment planning. An automatic ray-based or bounding-geometry-based collision detection algorithm can be used to detect overlap between possible treatment beams and the real-time position of image guidance hardware, as determined by manipulator joint encoders and/or by the optical or electromagnetic sensor attached to the probe itself.

As described above, in some embodiments, the manipulator can lock various degrees of freedom (using brakes or a motor) to prevent the operator from moving the probe to particular interfering positions, or give haptic feedback via the motors to push the probe away from interfering treatment beams. The probe can be initially placed without being attached to the manipulator, then subsequently attached to the manipulator at a later time once the initial imaging position is found. If the ultrasound imaging is performed after the CT scan, the couch and patient position are readily available. If the ultrasound is performed before the CT scan, the approximate couch position, LINAC position, and patient body position can be inferred based on the location of the tumor within the ultrasound images.

Further, as described above, in some embodiments, portions of the probe and the manipulator may be made of plastic and some may be made of metal. In such cases, the system can prioritize avoidance of these different materials in the treatment plan differently (i.e. to make it more important to avoid metal and less important or even unimportant to avoid plastic).

Because the potentially interfering positions are not static and the probe will move slightly with patient respiration during treatment, a range of motion for the probe and the manipulator can be built into software. This range of motion can be detected and saved during initial imaging (i.e. imaging with the ultrasound during treatment planning) using the manipulator encoders and/or the sensor attached to the ultrasound probe. Potential treatment beam and LINAC interferences can be taken into account for all positions in the captured range of motion.

Figure 27:
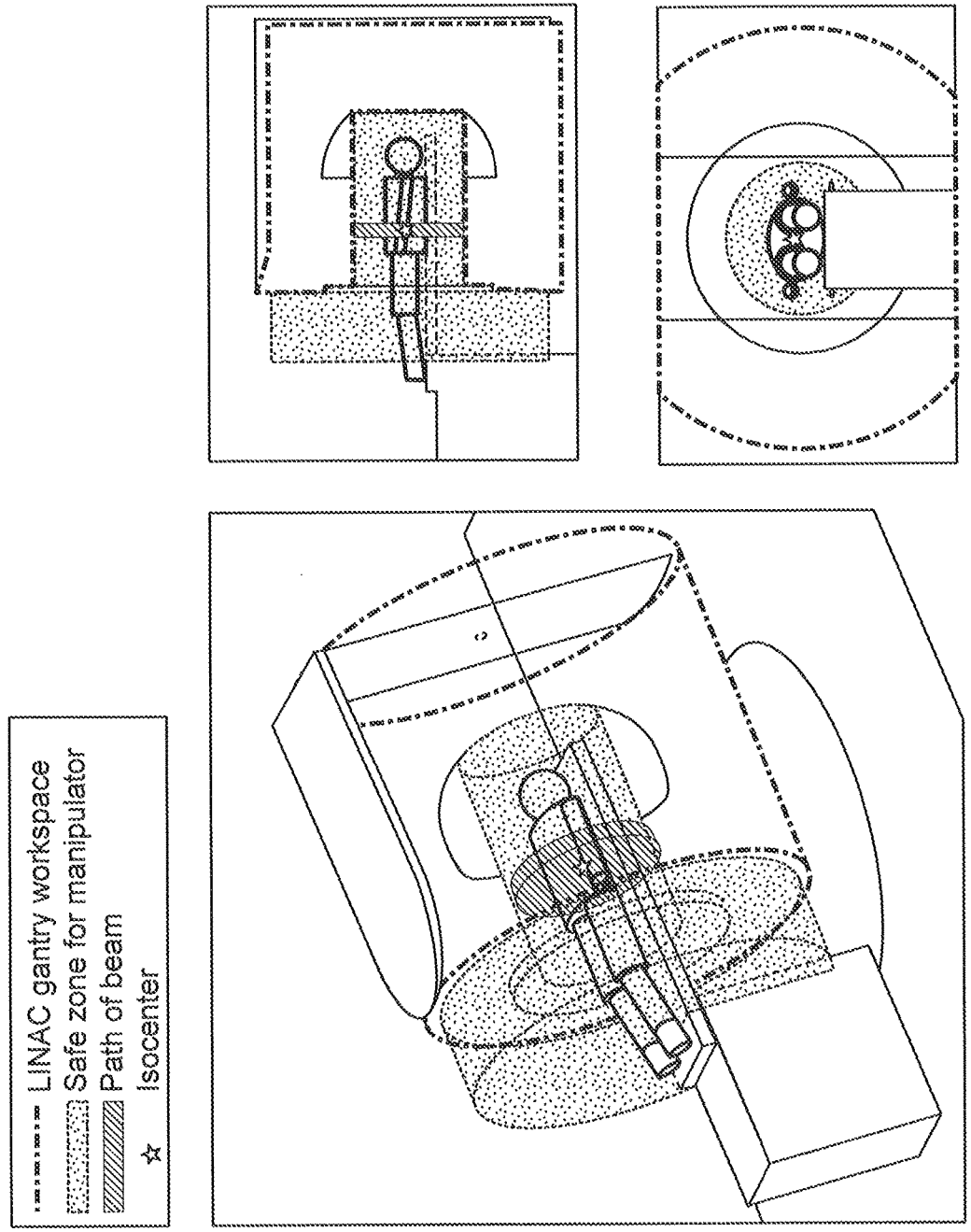
FIG. 27 shows a radiation treatment environment.
Figure 28:
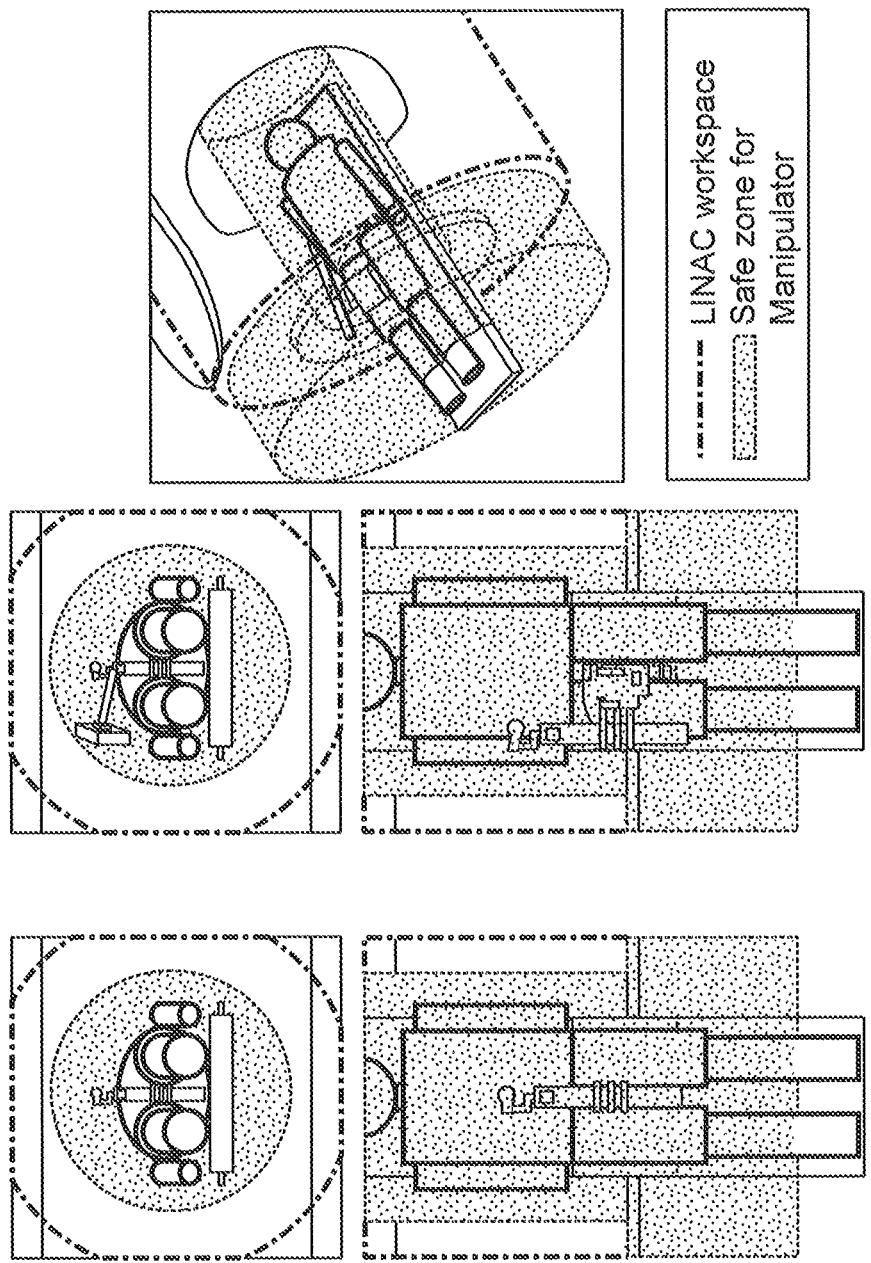
FIG. 28 shows a probe manipulator superimposed on the treatment environment.

Referring to FIGS. 27 and 28, in some embodiments, a 3D visualization of the probe and of the prospective treatment beam path can give the ultrasound operator an indication when the probe has entered the prospective treatment beam path during treatment planning. A similar 3D visualization can be used to indicate whether or not the manipulator will potentially interfere with the rotating linear accelerator gantry. The ultrasound probe and/or manipulator can be superimposed on LINAC and beam workspaces in real-time during the initial probe placement. Based upon this visualization, the operator can choose a location for the ultrasound manipulator and probe that will still gatherer the required images, but avoid positions that are most likely to be in the treatment path.

Similarly, in some embodiments, the system can give a warning when the probe and/or probe manipulator is placed in a position for treatment planning that may interfere with treatment beams. This warning can advantageously help the clinician determine where to place the manipulator and ultrasound to create the least interference with potential treatment beams.

In some embodiments, the detection mechanism described above can be used to find a probe position that will likely not interfere with treatment beams before the CT scan. That is, because the same amount of pressure should be placed on the patient by the ultrasound probe during both treatment and planning, in some embodiments, the ultrasound image and the CT image can be taken at the same time. To do so, the manipulator can automatically maintain the imaging position, slide the CT scanner couch into position, and collect concurrently a CT image and ultrasound image while the ultrasound probe is autonomously held against the patient.

Figure 29:
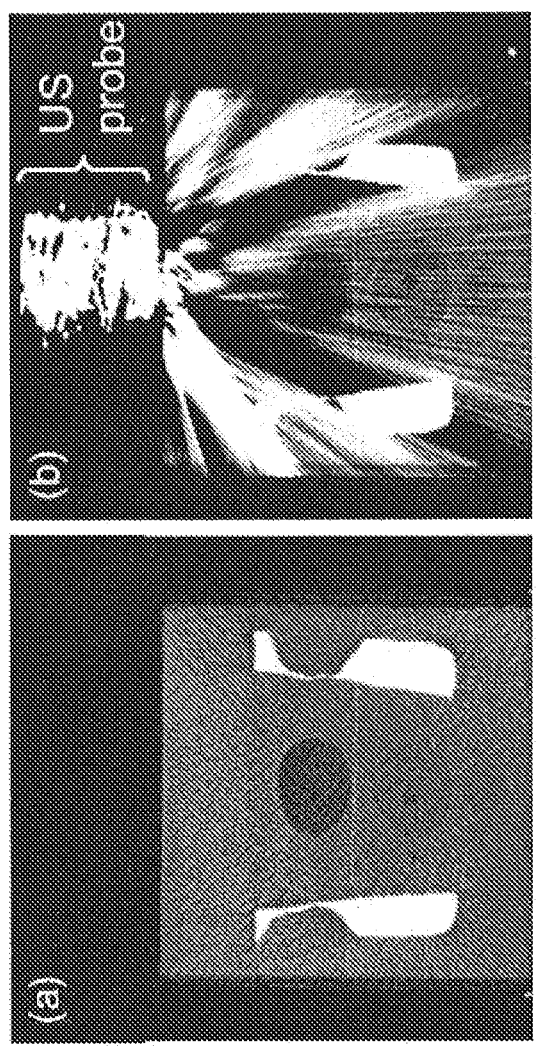
FIG. 29a shows a CT scan taken without a metallic ultrasound probe.
FIG. 29b shows a CT scan taken with a metallic ultrasound probe.

Taking ultrasound images concurrently with the CT scan can be made possible by ensuring that the probe will also not be in the path of the CT scanner. That is, if the probe is out of the beam directions, as in FIGS. 25(a) 25(c), the probe will also out of the primary path of the CT scanner. Note that the treatment planning system may need to tell the CT where to start and stop the "CT slices" because if the slices go too far past the tumor and touch the ultrasound probe (if in situation in FIGS. 25(a) and 25(c) and not using a dummy probe), metal artifacts could ensue. If the probe is potentially in the path of the treatment beam (and CT scanner), a dummy probe can be used during the CT, since metal artifacts in the ultrasound probe preclude its presence inside the CT imaging field, as shown in FIG. 29b.

In embodiments where ultrasound imaging is going to be performed after the CT scan (e.g., to use the CT to inform new ultrasound probe placements) for treatment planning, the CT scan itself can also be used to inform potential ultrasound probe placements that could avoid beam angles. After the CT scan, the CT can be analyzed to detect the presence of bone and/or bowel with gas. The bowel can be automatically or manually segmented to find out where potential gas will be located. The bone can be automatically or manually segmented as well. Imaging positions that produce images of the tumor that are not compromised by presence of bowel or bone between the ultrasound transducer and the tumor can be identified. Positions that further do not intersect with the treatment beams, and do not cause physical collisions between the image guidance hardware, LINAC, and patient, can be identified. In some embodiments, the tumor can be found on the CT by manual or automatic contouring, or by single-point annotation. A simulated ultrasound image can then be generated from any reasonable patient surface point to the tumor in the CT. These candidate imaging positions can be prioritized according to a certain set of weighted metrics before patient imaging. Metrics can include the predicted quality of the US image, potential physical collision of the probe manipulator with the LINAC gantry, and potential interference of radiation beams with image guidance hardware. Predicted US image quality will be primarily based on the degree of shadowing due to bone and/or gas present in US images simulated using CT information. Prospective physical collisions and beam interferences can be predicted based on the location of the tumor and prior models of the LINAC and beam geometry. Note that beam interference weightings will prioritize the US probe and manipulator differently, since metal (contained in the US probe) is harder to account for in the treatment planning process than plastic (material used in the distal portion of the manipulator).

The sonographer can be guided towards US probe placements in order of their weighted priority with assistance from the manipulator and a visualization application. Referring to FIG. 27, using the joint configuration of the manipulator and position sensing of the US probe, the image guidance hardware can be superimposed on a 3D geometric model of the treatment environment in real-time during probe placement. Prioritized probe placements can be displayed alongside the real-time hardware configuration to inform the sonographer where to move the probe. The manipulator's joints can lock sequentially as each joint is moved into proper configuration to achieve the desired probe position. The ultrasound image can have a real-time overlay with the prior CT data to further help find the correct ultrasound imaging position.

If prior imaging information is not available, a low-dose CT scan can be performed to inform the probe placements. The method can then involve acquiring low-dose CT scan, using techniques as above to find best probe positioning candidates, then performing higher-dose CT scan with probe or dummy probe in position for treatment planning purposes.

Further, in some embodiments, after placing the ultrasound probe in position based on the prior imaging information (e.g. CT), the manipulator can apply different pressures and record the anatomy deformation and resulting lesion displacement in the spatially localized ultrasound images. A map of lesion location vs. probe pressure can be formed. The first CT scan (without the ultrasound probe and manipulator) can be deformed according to the map and the specific probe pressure applied, so a second CT scan is not needed. Alternatively, the contours on the CT scan (lesion, surrounding anatomy, patient surface, etc.) can be displaced/deformed instead of the CT scan itself. Either way, this approach enables accounting for the displaced/deformed anatomy and lesion location during the treatment planning due to the probe pressure, but does not require a CT scan with the manipulator applying pressure at the same time.

The effects of probe pressure can be minimized by using a large cup (as in FIG. 7b) or an acoustic pad to spread out the pressure of the transducer over a larger area, as described above. The contact between the bottom of the cup and the patient is advantageously repeatable between the planning CT scan and the actual treatment. When an imaging probe position is found during planning, if that position would interfere with the CT scan and cause artifacts, it is easy to snap the probe out of the cup and perform the CT scan, while still maintaining the correct pressure. It is easy to have the manipulator achieve the same position and pressure for the cup during treatment (since the force and joint positions were saved during planning), so during treatment the manipulator positions the cup, then the probe is easily snapped in. This setup yields an easy and repeatable way for the correct pressure to be maintained with the dummy probe during CT scan after the ultrasound imaging is performed.

Further, the effects of probe pressure can also be minimized by commanding the manipulator to reduce the probe pressure until the image quality is reduced, then increasing the pressure just past this threshold. In this way, the manipulator can apply the minimum pressure required to maintain a stable ultrasound image, minimizing the deformation to anatomy. If these techniques are used, then the manipulator may not need to apply pressure to the patient during the CT scan at all, since the pressure during treatment will be minimized.

In some embodiments, multiple ultrasound imaging positions may be found that avoid the treatment beam. These positions can be saved in case some positions are obstructed at the time of treatment due to bowel gas or other dynamic factors. Note that depending on the depth of the tumor, multiple CT scans may need to be performed if deformation differences between different probe positions are a concern.

The ultrasound technician performing the initial scan can thus use the techniques described herein to their advantage to help identify the best probe placements that yield: (1) viable ultrasound imaging windows that are not compromised by bowel, bone, or other obstructions; (2) probe and manipulator positions that do not interfere with treatment beams; and (3) probe and manipulator positions that do not cause physical collisions between image guidance hardware and the LINAC.

In some embodiments, in addition to or in place of choosing a manipulator/probe location that will avoid the positions most likely to interfere with beams, beam directions and shapes can be chosen during the treatment planning process that will not interfere with the probe manipulator or ultrasound probe. That is, for some patients and certain cancer sites, the presence of ribs, bowel gas, fatty tissue, or other obstructions could restrict probe placement to areas that may interfere with treatment beams. Potential interferences can thus be taken into account during the beam planning process.

Figure 24:
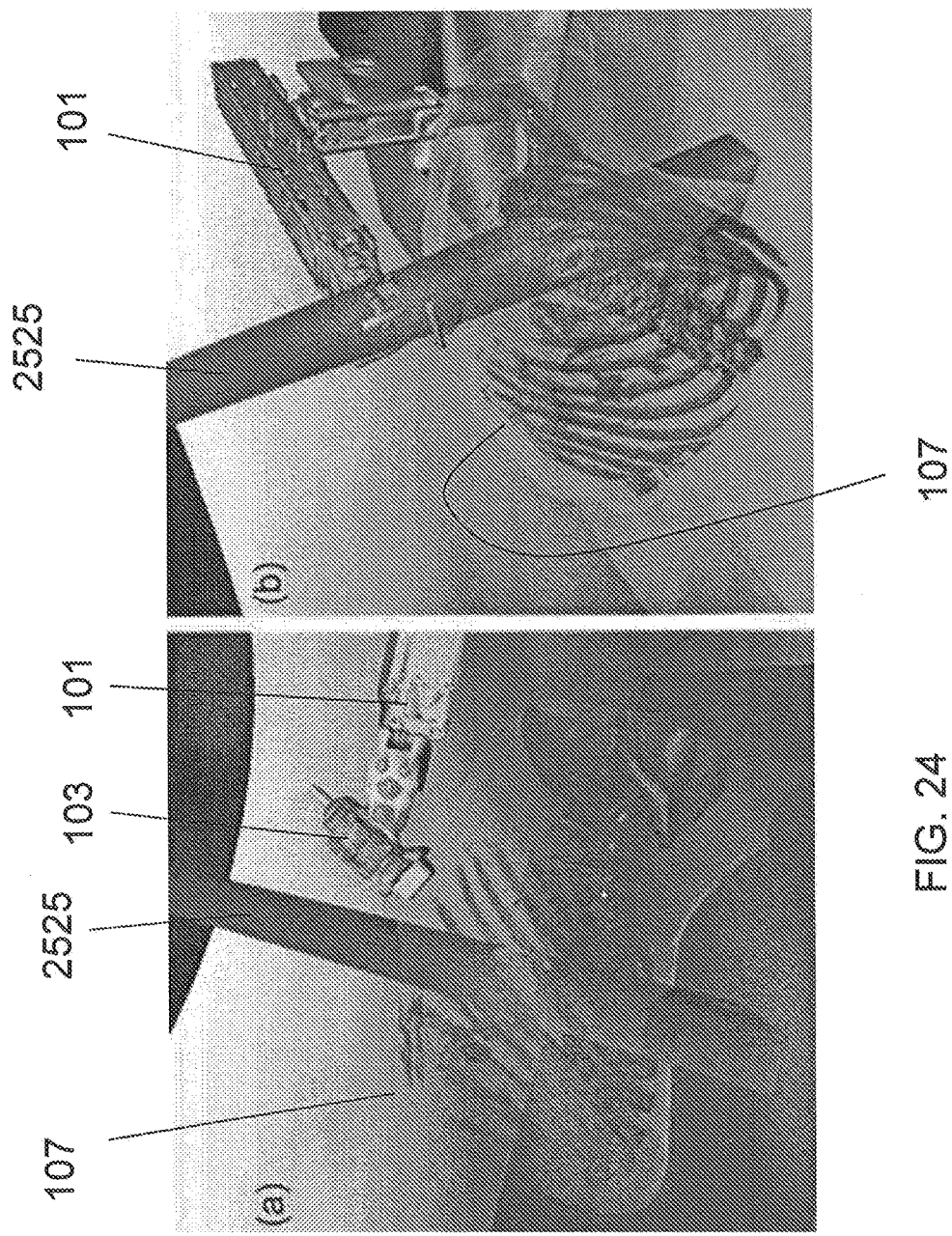
FIGS. 24a and 24b show 3-D ultrasound images and: (a) no interference of the probe or probe manipulator with radiation beams; or (b) interference of the probe and probe manipulator with radiation beams.

In some embodiments, a software program that enables 2D and 3D visualization of the LINAC, couch, treatment beams, manipulator, ultrasound probe, and patient can be used to quantify which beam angles and shapes potentially interfere with image guidance. The ultrasound probe placement and manipulator position used to image target sites during the planning process can be saved using the manipulator's joint encoders and utilized to precisely place the image guidance hardware within the virtual environment. FIG. 26 shows a screenshot of the 2D viewer, and FIG. 24 shows examples from the 3D viewer.

In some embodiments, radiation beams can be projected outward in 3D from the LINAC head for each potential LINAC gantry angle. Ray-based or bounding-geometry-based collision detection methods can be implemented to detect geometric interference between the projected radiation beams and the image guidance hardware models. During the treatment planning process, these interfering beams can be avoided. Furthermore, potential collisions between the probe manipulator, linear accelerator, and treatment couch can be visualized in advance and avoided using the software. The software can further inform and investigate different positions, configurations, or placements of the probe manipulator relative to the patient such that the manipulator does not interfere with critical radiation beams in the treatment planning process.

In some embodiments, when the patient goes into treatment, the software or manipulator itself can guide the therapist to put probe exactly where it was during planning. However, in such instances, the anatomy configuration can be slightly different (due to bowel gas or other dynamic factors), so the ultrasound probe position may need to be slightly different. Accordingly, a motion uncertainty envelope can be placed around the probe position(s) found during planning. This entire envelope can be avoided during the beam planning process. In some embodiments, the motion envelope can be predicted based upon a CT scan. For example, if the position of the bowels can be determined based on the CT scan, then a potential location for gas is known, and the software can use this information to adjust the motion envelope accordingly.

In some embodiments, treatment planning to avoid the probe can be made easier by using a dummy probe that includes different densities—one plastic to designate plastic areas on the real probe, and another plastic with a different density to indicate metal areas on the real probe. This way, in the CT scan, the parts that would contain metal during treatment would be obvious, making it easier to choose radiation beams that avoid the most relevant parts of the probe. That is, while it can be difficult to irradiate through metal, it can be much to irradiate through plastic. Accordingly, the treatment planning software can be used to avoid only the metal parts of the ultrasound probe while irradiating through plastic parts of the probe and the manipulator if needed. A probe with different densities allows us to easily see or automatically identify the "metal" areas of the probe (which are actually plastics of different densities in the dummy probe). This way, the likely location of the metal areas during treatment can be easily identified during treatment planning, allowing those locations to be taken into account when developing the treatment plan.

Thus, there can be a software environment that contains the manipulator, ultrasound transducer, radiation beams, linear accelerator, patient CT model, etc. The interference between the radiation beams and the manipulator/US probe in 3D can be visualized or located in a set of orthogonal planes in the software and/or the interference can be automatically detected using existing ray-based or bounding-geometry-based collision detection algorithms. The position of the manipulator within the software environment can be determined based on image segmentation of the manipulator links in the CT scan and/or saved joint position information for the manipulator during the planning stage. The position of the ultrasound probe in the software is determined via 3D tracking, manipulator joint info, or segmentation.

In some embodiments, non-coplanar beam arrangements and other non-traditional planning can be used to avoid interference between the radiation beams and the hardware. In traditional radiation therapy, the patient lies in a fixed position on the couch, and the linear accelerator rotates around it—doing so ensures that the patient does not have to be reimaged with CT or X-rays to find the appropriate position. However, with a system that includes continuous ultrasound imaging during radiation, additional CT imaging can be avoided. Rather, because the ultrasound produces nonionizing imaging of the target, both the couch (with the manipulator attached thereto) and the linear accelerator can be moved during treatment in order to achieve a wider range of beam angles and non-coplanar beam arrangements. Movement of the couch can potentially allow for the accommodation of a wider range of patients (such as larger patients where couch might need to be shifted down) and can allow for the achievement of better dose distributions. The 3D software environment thus allows the physicist to test various couch movements in order to achieve non-traditional beam angles. When the couch is moved, physical collisions become very important to avoid, so the collision-detection capabilities of the software can be used to detect potential physical interferences between patient, guidance hardware, LINAC gantry, and couch, along with potential beam interferences In some embodiments, if multiple ultrasound probe placements are found during the planning process, then the treatment plan can include one or more of the probe placement positions. For example, if two positions interfering with treatment beams are found, then the probe and probe holder (manipulator) can be physically moved (manually or automatically) mid-treatment in order to avoid the respective beams. This way, the treatment could be planned using all beam angles, knowing that the probe position would be moved in order to avoid beams as they are delivered during treatment.

In some embodiments, since the treatment imaging position might not be identical to the planned position, a warning system can be put in place such that probe and manipulator positions are ensured to not interfere with the precise planned beams (if their positions exceed the motion uncertainty envelope planned for). The warning system could involve manipulator feedback and/or visualization as previously described for potential interferences.

The treatment planning techniques described herein could be used, for example, with the ultrasound systems described above. Alternatively, the techniques described herein could be used to enable ultrasound imaging concurrent with other imaging and therapy procedures, including but not limited to Cyberknife radiosurgery, proton therapy, particle therapy, projection x-ray imaging (including fluoroscopy for catheter and/or needle guidance), computed tomography (CT) imaging, magnetic resonance imaging (MRI), photon emission tomography (PET) imaging, and other procedures that could benefit from real-time ultrasound imaging. Further, it should be understood that the ultrasound imaging described herein could be substituted with other portable imaging modalities, such as photoacoustic imaging, optical imaging, microscopy, imaging with gamma cameras, or portable x-ray imaging.

Specific examples of avoiding collision between the manipulator/probe and radiation beams are described below. In one embodiment, the effect of restricting beam angles on a prostate was evaluated, and in another embodiment, the effect of restricting beam angles on a liver was evaluated.

The virtual environment was used to select beam angles that would not interfere with guidance hardware within each plan. Since the manipulator was not used for imaging these two patients before treatment delivery, the manipulator and ultrasound probe were placed within the virtual environment by visually inspecting the patient's CT scan and placing the hardware such that a clear ultrasound imaging window was available to the tumor (no imaging through bowel or bone).

Example 1—Liver Plan

Figure 30:
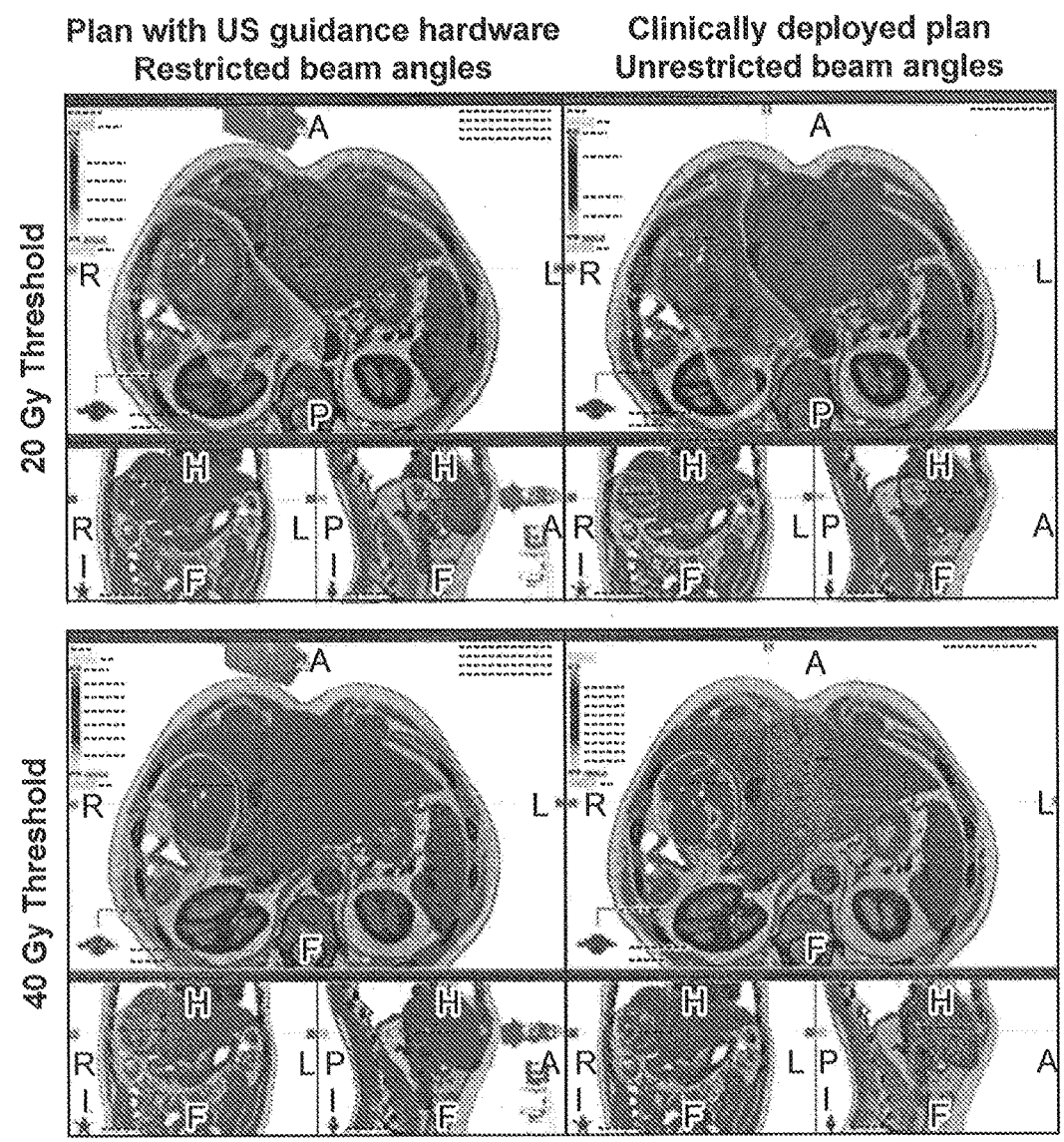
FIG. 30 shows treatment plans with restricted beam angles and without.
Figure 31:
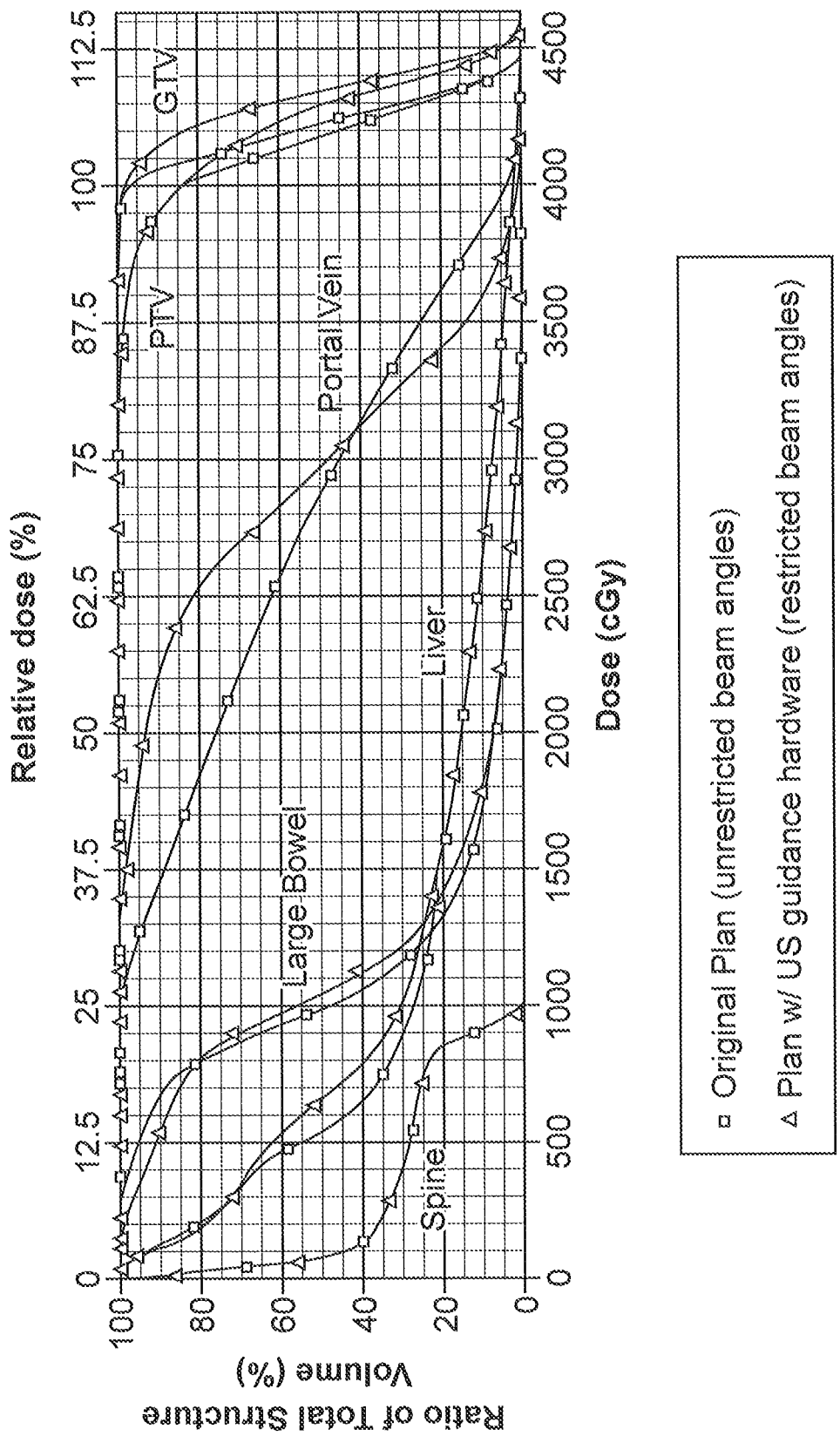
FIG. 31 shows exemplary radiation dose volume histograms.

A clinically-delivered arc therapy plan for a liver cancer patient was re-optimized in order to avoid beam angles interfering with image guidance hardware. In arc therapy, instead of a delivering a discrete set of radiation beams, the LINAC continuously rotates while delivering radiation at a continuum of angles. A 120 degree arc segment was avoided in the re-optimized plan. FIG. 30 shows the clinically deployed plan and the plan with restricted angles, using a 20 Gy threshold dose (top) and 40 Gy threshold dose (bottom). The dose volume histograms are shown in FIG. 31.

The dose distributions between the two plans appear very similar in FIG. 30. In FIG. 31, dose delivered to the PTV and GTV is slightly higher in the new plan with restricted beam angles. Normal tissue dose for the spine, liver, and large bowel are very close between plans. For the portal vein, a larger volume receives relatively low radiation doses in the plan with restricted angles, but a smaller volume receives high radiation roses, yielding a clinically ambiguous effect on portal vein toxicity. Overall, restricting beam angles does not appear to have detrimental effects on the achieved radiation dose distribution for this liver cancer patient.

Example 2—Prostate Plan

In this investigation, the effect of restricting the beam angles in a prostate intensity modulated radiation therapy (IMRT) plan to directions that do not interfere with the centrally located abdominal ultrasound probe and manipulator was explored. This strategy was motivated by observed intra- and inter-institutional variability of clinical prostate IMRT techniques in terms of beam number and configurations. Field arrangements that include an anterior or posterior beam have been reported, with the inclusion of the latter being preferable. In light of the success of these alternative planning techniques, a 7-beam clinical plan for a prostate IMRT patient was re-optimized with a 7-beam configuration that excluded a 90° anterior sector, avoiding the ultrasound probe and manipulator hardware. Furthermore, the potential benefit of introducing real-time image-guidance, despite the elimination of certain beam directions, was further investigated by reducing the planning target volume (PTV) margin by 2 mm and re-optimizing the plan with restricted beam angles. For comparison, all plans were normalized to maintain initial clinical target objectives: 95% coverage of the respective PTV volumes by the 100% (prescription) isodose surface, and 100% coverage of the GTV volume by the prescription isodose surface.

Figure 32:
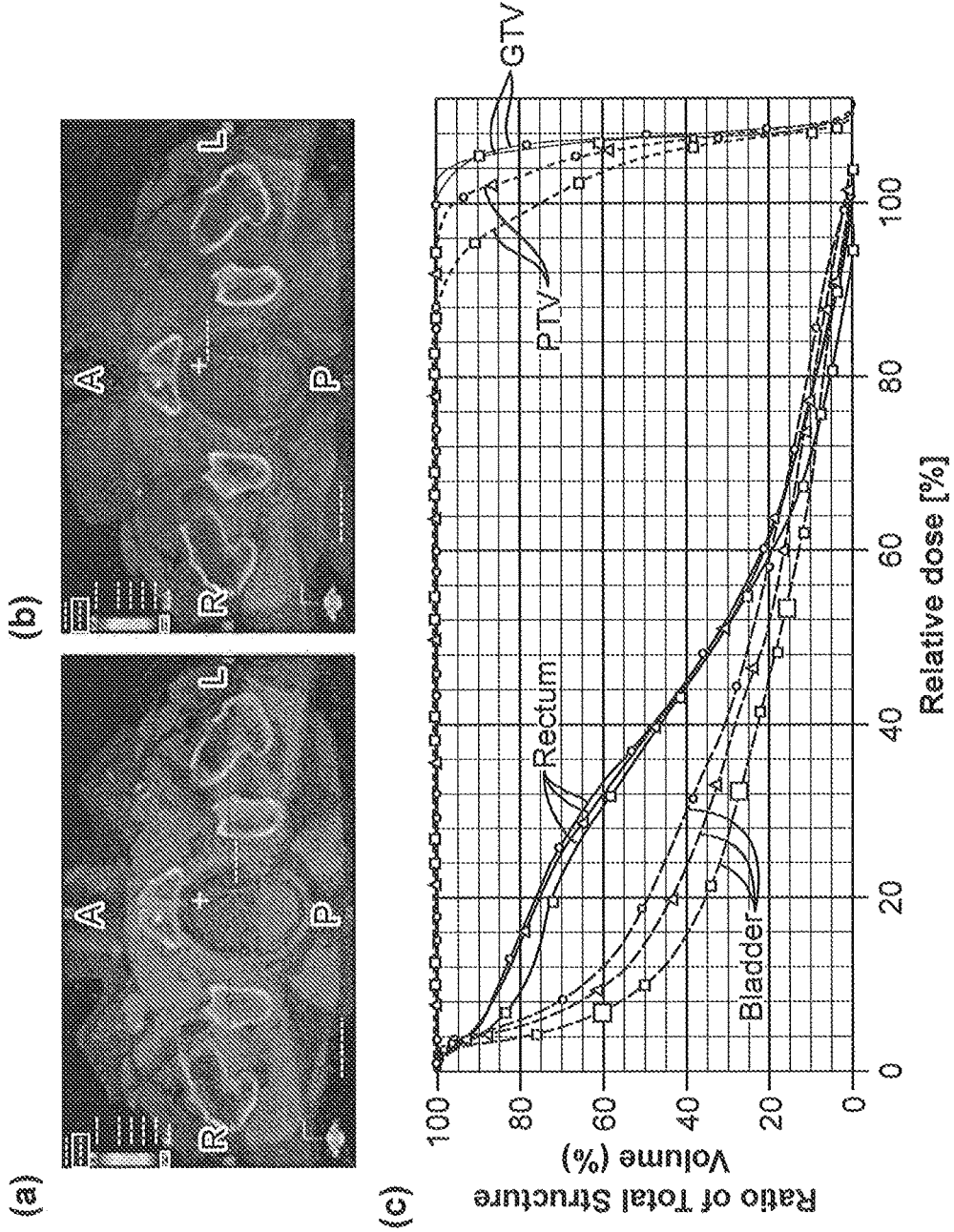
FIG. 32a shows an exemplary radiation treatment plan.
FIG. 32b shows another exemplary radiation treatment plan.
FIG. 32c shows a dose volume histogram for the treatment plans of FIGS. 32a and 32b.

FIG. 32 illustrates (a) the original clinical prostate IMRT plan with (b) the alternative IMRT plan that excludes beam directions that can interfere with the ultrasound transducer. The dose-volume histogram (DVH) comparison shown in 32(c) demonstrates that the DVHs for the two plans are virtually identical. With margins reduced by 2 mm, as could be enabled by real-time imaging, GTV coverage was identical while notable reductions of bladder and rectal volumes exposed to large doses were possible in FIG. 32 (c).

Delivering Radiation Through the Manipulator

Figure 33:
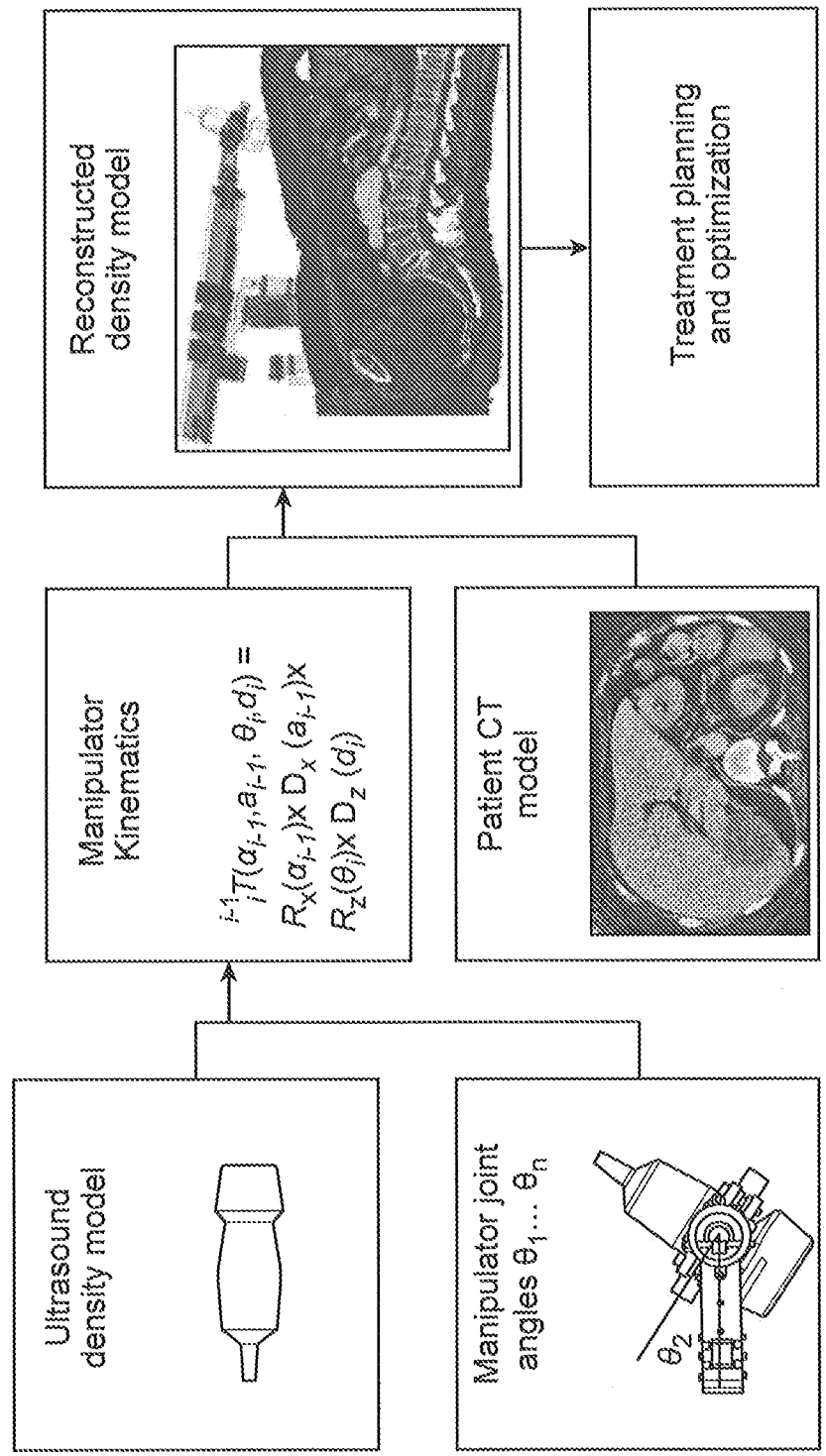
FIG. 33 is a flow chart for delivering radiation through a manipulator.

In another embodiment, radiation can be delivered through the manipulator and transducer by taking into account the density of the manipulator and transducer. Referring to FIG. 33, in one embodiment, the patient is scanned with CT using the manipulator and dummy probe (or probe specifically designed with non-metallic materials). This information can be merged with a density model of the ultrasound probe (using the known location of the ultrasound probe with respect to the manipulator) to create a full patient-specific density model of the setup as it will appear during treatment. The ultrasound probe density model can be created by independently scanning the probe with CT. If metal artifacts are too obstructive in the probe scan, a density model can be constructed based on known probe material properties and geometry. The full patient-specific density model (including manipulator and ultrasound probe hardware) is then input to radiation planning software for treatment planning and optimization.

As noted above, in some embodiments, radiation can delivered through the manipulator and transducer by taking into account the densities of the manipulator and transducer. In one embodiment, the patient is scanned with CT using the manipulator and dummy probe (or probe specifically designed with non-metallic materials). As shown in FIG. 33, this information can be merged with a density model of the ultrasound probe (using the known location of the ultrasound probe with respect to the manipulator) to create a full patient-specific density model of the setup as it will appear during treatment. The ultrasound probe density model can be created by independently scanning the probe with CT. If metal artifacts are too obstructive in the probe scan, a density model can be constructed based on known probe material properties and geometry. The full patient-specific density model (including manipulator and ultrasound probe hardware) is then input to radiation planning software for treatment planning and optimization.

In some embodiments, the dummy probe can be designed with specific features to make it easy to remove from the original CT scan and insert the density model of the real transducer. For example, it can contain a pattern of different densities that make its position and orientation very easy to identify in the CT scan. In some embodiments, the density model can be produced by a CAD program with prior knowledge of the probe construction. Alternatively, the density model can be formed using tomotherapy or megavoltage CT/cone beam CT, which advantageously does not produce metal artifacts.

There may be slightly different probe/manipulator position at time of treatment than during planning. If positions are too different than positions that planned for, then the dose plan may no longer be valid. Accordingly, in some embodiments, a warning system can be put in place to indicate such off-set during treatment.

Removing the Manipulator During Portions of Radiation Treatment

In another embodiment, the manipulator is physically removed during portions of radiation therapy to avoid interference with the therapy. That is, the guidance system can be physically retracted from the path of the particular beam(s) for which it interferes. Interference is detected a-priori using the collision software described above. The manipulator and ultrasound probe can be retracted manually by the radiation therapist or automatically (remotely) using a motor on the probe manipulator. While this introduces localization uncertainty during the delivery of interfering beam(s), this strategy still offers intra-fractional guidance capabilities for the most significant part of the treatment, as advanced EBRT techniques (IMRT, SBRT) usually involve a large number of beams.

Other Treatment Planning Related-Issues

Another challenge associated with using an ultrasound system during radiation beam therapy is determining the exact relationship between the ultrasound image and the CT scan during treatment planning and radiotherapy. In one embodiment, the position of the ultrasound probe can be tracked for purposes of spatial registration using joints of a mechanical arm or manipulator. The joints could be used alone, or in combination with other tracking means. For example, an optical tracker could provide the initial position of the probe in the room, and then during radiotherapy, the manipulator joints could track small movements of the probe relative to the initial position.

In another embodiment, the ultrasound images can be acquired concurrent with the acquisition of the CT image during treatment planning. By tracking the US probe (using the manipulator joints or another 3D tracker or both), the US images can be spatially localized with respect to the CT or MRI images, and thus fused with these images without the need for software-based fusion. The ultrasound image that is referenced to the CT or MRI image can then be used as a reference image for tracking during radiotherapy or other procedures.

CONCLUSION

The systems described herein can be applied in many radiation treatment scenarios. In one embodiment, the manipulator places the ultrasound probe against the patent's abdomen in order to perform transabdominal imaging during radiation treatment. In addition, the ultrasound system described herein is not limited to use with a conventional C-arm LINAC; it can also be used with the Cyberknife radiosurgery robot or tomotherapy systems. In fact, the design elements of the probe manipulator, the virtual collision detection environment, and the tissue tracking algorithms can be used as hands free image guidance tools in many procedures other than radiation therapy as well, such as needle insertion, brachytherapy, catheter placement, surgery, robotic surgery, etc.

Further, the ultrasound system described herein can be integrated with conventional linear accelerators and/or can be used with standard ultrasound transducers.

Although the imaging system has been described herein performing radiation in conjunction with ultrasound imaging, it is to be understood that other imaging modalities can be used with or in place of the ultrasound system, including CT or MRI imaging.

Further, although the treatment planning aspects have been described as including a CT scan, other imaging scans are possible, such as ultrasound, MRI, positron emission tomography (PET), or other volumetric imaging modalities.

Moreover, although treatment has been described above as including radiation therapy, it is to be understood that other medical procedures, treatments, or therapies can be used with or in place of the radiation therapy described herein.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of planning the delivery of a radiation therapy, comprising:
   positioning an imaging probe manipulator having an imaging probe connected thereto such that the imaging probe is in a desired geometrical position for taking a first image of a patient's target anatomy with a first imaging modality;
   conducting a medical imaging scan of a portion of a patient's anatomy using a second imaging modality that is different from the first imaging modality to obtain a second image, wherein the probe or an inoperable probe is in the desired geometrical position during the conducting step;
   using the second image to develop a radiation therapy delivery plan that allows for delivering radiation to the patient's target anatomy while imaging the patient's target anatomy with the imaging probe, the radiation plan reducing or eliminating effects of interference between radiation beams and the imaging probe on the patient's radiation dose; and
   imaging a portion of the patient's target anatomy with the imaging probe during radiation therapy performed according to the radiation therapy delivery plan, wherein the imaging probe is in the desired geometrical position during the imaging step.

2. The method of claim 1, wherein the imaging probe manipulator has a plurality of joints, and wherein positioning the imaging probe comprises locking at least some of the joints in place.

3. The method of claim 2, further comprising storing positions of the joints after locking at least some of the joints in place.

4. The method of claim 1, wherein the positioning step or the imaging step is determined using knowledge of a geometrical configuration of a radiation delivery system to be used to deliver a therapy to the patient's target anatomy.

5. The method of claim 1, wherein the positioning step or the imaging step is determined using knowledge of a geometrical configuration of a potential radiotherapy beam arrangement to be used during therapy delivery to the patient's target anatomy.

6. The method of claim 1, further comprising using simulated probe images of a portion of the patient's target anatomy to inform positioning the probe prior to radiation therapy.

7. The method of claim 1, wherein a low-dose CT scan is used to simulate images from the probe.

8. The method of claim 1, further comprising using bone or gas data from the imaging scan of a portion of the patient's target anatomy to inform positioning the probe prior to conducting radiation therapy.

9. The method of claim 1, where in the positioning step, the manipulator locks or provides resistance to one or more joints to prevent the probe operator from moving the probe to particular positions that could interfere with the treatment delivery device or radiation beams.

10. The method of claim 1, where in the positioning step, the manipulator actively controls one or more of the joints to push the probe towards particular positions that are determined to be suitable according to treatment geometry or simulated images.

11. The method of claim 1, further comprising using a visualization platform coupled to the manipulator to provide position, pose, or pressure information during the positioning, imaging, or planning steps.

12. The method of claim 1, further comprising using a visualization platform coupled to the manipulator to detect potential imaging probe and imaging probe manipulator interference with one or both of a physical treatment system component and/or a planned treatment beam to be used in later radiation therapy of the patient target anatomy.

13. The method of claim 12, further comprising using an output from the visualization platform for positioning of the imaging probe and the imaging probe manipulator to avoid a physical treatment system component and/or the planned treatment beam.

14. The method of claim 12, further comprising using a plurality of outputs from the visualization platform for positioning of the imaging probe and the imaging probe manipulator, each one of the outputs corresponding to a positioning of the probe and manipulator for a portion of the radiation therapy such that for beams during that portion the probe and the manipulator avoid the treatment system component and the planned treatment beam.

15. The method of claim 12, further comprising delivering a first portion of a radiation therapy to a patient where the manipulator and the probe are in one of the corresponding outputs and delivery of a second portion of a radiation therapy to a patent where the manipulator and the probe are in another one of the corresponding outputs.

16. The method of claim 1, wherein the conducting step is performed with an inoperable probe in the desired geometrical position, the inoperable probe comprising non-metallic materials that is coupled to the imaging probe manipulator.

17. The method of claim 1, wherein the conducting step is performed with an inoperable probe in the desired geometrical position, wherein the inoperable probe includes different densities to indicate different densities in the actual imaging probe, and wherein the method further includes avoiding areas of high density during the planning so that areas of high density can be avoided during treatment.

18. The method of claim 16, wherein the imaging probe is connected to the imaging probe manipulator through a connector, the connector including a cup having a gel or fluid therein.

19. The method of claim 1, wherein the conducting step is performed with an imaging probe coupled to the imaging probe manipulator and the medical imaging scan of a portion of a patient's anatomy includes a portion of a density model of the imaging probe.

20. The method of claim 1, wherein the conducting step is performed with an imaging probe holder coupled to the imaging probe manipulator and the medical imaging scan of a portion of a patient's anatomy includes a portion of a density model of an imaging probe to be coupled to the imaging probe holder during a later delivery of radiation therapy.

21. The method of claim 1, further comprising applying pressure to the patient target anatomy using a plurality of probe pressures, recording deformations of the patient target anatomy resulting from each pressure in the plurality of pressures, and incorporating information from the deformations to computationally deform the medical imaging scan to reproduce deformations expected during treatment.

22. The method of claim 21, further comprising modifying the imaging data collected during the conducting step based on one or more of the recorded deformations.

23. The method of claim 1, wherein the second imaging modality is magnetic resonance imaging (MRI), positron emission tomography (PET), or computed tomography (CT).

* * * * *